US007473770B2

(12) United States Patent
Harada et al.

(10) Patent No.: US 7,473,770 B2
(45) Date of Patent: Jan. 6, 2009

(54) CYNOMOLGUS MONKEY DICKKOPF-4, NUCLEOTIDES ENCODING SAME, AND USES THEREOF

(75) Inventors: Shun-ichi Harada, Ambler, PA (US); Viera Kasparcova, Collegeville, PA (US); Helmut Glantschnig, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 157 days.

(21) Appl. No.: 10/579,596

(22) PCT Filed: Nov. 12, 2004

(86) PCT No.: PCT/US2004/037799

§ 371 (c)(1), (2), (4) Date: May 17, 2006

(87) PCT Pub. No.: WO2005/049797

PCT Pub. Date: Jun. 2, 2005

(65) Prior Publication Data

US 2007/0087384 A1 Apr. 19, 2007

Related U.S. Application Data

(60) Provisional application No. 60/520,569, filed on Nov. 17, 2003.

(51) Int. Cl.
*C07H 21/04* (2006.01)
*C12P 21/06* (2006.01)

(52) U.S. Cl. .................... 536/23.5; 536/22.1; 536/23.1; 536/23.4; 435/69.1; 435/7.1; 435/7.2; 435/69.7

(58) Field of Classification Search ....................... None
See application file for complete search history.

(56) References Cited

U.S. PATENT DOCUMENTS

| | | | | |
|---|---|---|---|---|
| 2003/0068312 | A1 | 4/2003 | McCarthy | |
| 2003/0181660 | A1 | 9/2003 | Todd et al. | |
| 2004/0038860 | A1* | 2/2004 | Allen et al. | 514/2 |
| 2005/0069915 | A1 | 3/2005 | McCarthy | |
| 2005/0079173 | A1 | 4/2005 | Niehrs et al. | |

FOREIGN PATENT DOCUMENTS

| | | |
|---|---|---|
| WO | WO 98/46743 | 10/1998 |
| WO | WO 98/46755 | 10/1998 |
| WO | WO 99/22000 | 5/1999 |
| WO | WO 00/52047 | 9/2000 |
| WO | WO 02/092015 | 11/2002 |

OTHER PUBLICATIONS

Bafico et al., Nature Cell Biology, vol. 3 (2001), pp. 683-686, "Novel mechanism of Wnt signalling inhibition mediated by Dickkopf-1 interaction with LRP6/Arrow".

Bennett et al., J. of Biol. Chem., vol. 277 (2002), pp. 30998-31004, "Regulation of Wnt signaling during adipogenesis".

Boyden et al., N. Eng. J. of Med., vol. 346 (2002), pp. 1513-1521, "High bone density due to mutation in LDL-receptor-related protein 5".

Davidson et al,. Development, vol. 129 (2002), pp. 5587-5596, "Kremen proteins interact with Dickkopf1 to regulate anteroposterior CNS patterning".

Fujino et al., PNAS, vol. 100 (2003), pp. 229-234, "Low-density lipoprotein receptor-related protein 5 (LRP5) is essential for normal cholesterol metabolism and glucose-induced insulin secretion".

Glinka et al., Nature, vol. 391 (1998), pp. 357-362, "Dickkopf-1 is a member of a new family of secreted proteins and functions in head induction".

Gong et al., Cell, vol. 107 (2001), pp. 513-523, "LDL receptor-related protein 5 (LRP5) affects bone accrual and eye development".

Hey et al., Gene, vol. 216 (1998), pp. 103-111, "Cloning of a novel member of the low-density lipoprotein receptor family".

Hsu et al., Molecular and Cellular Biol., vol. 18 (1998), pp. 4807-4818, "Modulation of transcriptional regulation by LEF-1 in response to Wnt-1 signaling and association with beta-catenin".

Katagiri et al., J. of Cell Biology, vol. 127 (1994), pp. 1755-1766, "Bone morphogenetic protein-2 converts the differentiation pathway of C2C12 myoblasts into the osteoblast lineage".

Kato et al., J. of Cell Biology, vol. 157 (2002), pp. 303-314, "Cbfa1-independent decrease in osteoblast proliferation, osteopenia, and persistent embryonic eye vascularization in mice deficient in Lrp5, a Wnt coreceptor".

Krupnik et al., Gene, vol. 238 (1999), pp. 301-313, "Functional and structural diversity of the human Dickkopf gene family".

Li et al., The EMBO Journal, vol. 18 (1999), pp. 4233-4240, "Axin and Frat1 interact with Dvl and GSK, bridging Dvl to GSK in Wnt-mediated regulation of LEF-1".

Little et al., Am. J. Hum. Genet., vol. 70 (2002), pp. 11-19, "A mutation in the LDL receptor-related protein 5 gene results in the autosomal dominant high-bone-mass trait".

Magoori et al, J. of Biol. Chem., vol. 278 (2003), pp. 11331-11336, "Severe hypercholesterolemia, impaired fat tolerance, and advanced atherosclerosis in mice lacking both low density lipoprotein receptor-related . . . ".

Mao et al., Gene, vol. 302 (2003), pp. 179-183, Kremen2 modulates Dickkopf2 activity during Wnt/LRP6 signaling.

(Continued)

*Primary Examiner*—David S Romeo
*Assistant Examiner*—Daniel C Gamett
(74) *Attorney, Agent, or Firm*—Patricia L. Chisholm; Valerie J. Camara

(57) ABSTRACT

The cynomolgus monkey Dickkopf-4 (cDkk-4) protein, isolated nucleic acid molecules which encode the cDkk-4 protein, and recombinant vectors and hosts comprising DNA encoding the cDkk-4 protein are disclosed. Also disclosed are methods for identifying analytes which interfere with the interaction between the cDkk-4 protein and a homologous or heterologous Dkk receptor and analytes which interfere with the interaction and stimulate bone formation. Analytes identified using the methods are useful for treating osteoporosis and other bone loss disorders.

12 Claims, 9 Drawing Sheets

OTHER PUBLICATIONS

Mao et al., Molecular Cell, vol. 7 (2001), pp. 801-809, "Low-density lipoprotein receptor-related protein-5 binds to axin and regulates the canonical Wnt signaling pathway".

Mao et al., Nature, vol. 411 (2001), pp. 321-325, "LDL-receptor-related protein 6 is a receptor for Dickkopf proteins ".

Mao et al., Nature, vol. 410 (2002), pp. 664-667, "Kremen proteins are Dickkopf receptors that regulate Wnt/beta-protein signaling".

Patel et al., N. Eng. J. Med., vol. 346 (2002), pp. 1572-1574, "Regulation of bone formation and vision by LRP5".

Semenov et al., Current Biology, vol. 11 (2001), pp. 951-961, "Head inducer Dickkopf-1 is a ligand for Wnt coreceptor LRP6".

Sjolander et al., Anal. Chem., vol. 63 (1991), pp. 2338-2345, "Integrated fluid handlding system for biomolecular interaction analysis".

Szabo et al., Current Opin. in Structural Biol., vol. 5 (1995), pp. 699-705, "Surface plasmon resonance and its use in biomolecular interaction analysis (BIA)".

Yuan et al., J. of Biol. Chem., vol. 274 (1999), pp. 30419-30423, "Suppression of glycogen synthase kinase activity is not sufficient for leukemia enhancer factor-1 activation".

Yamaguchi et al., Biochem. and Biophys. Res. Comm., vol. 220 (1996), pp. 366-371, "Effects of BMP-2, BMP-4, and BMP-6 on osteoblastic differentiation of bone marrow-derived stromal cell lines, ST2 and . . . ".

* cited by examiner

ATGGCGGCGG CCGTCCTGCT GGGACTGAGC TGGCTCTGCT CTCCCCTGGG AGCTCTGGTC 60
CTGGACTTCA ACAACATCAG GAGCTCTGCT GACCTGCTTG GGGCCCGGAA GGGCTCACAG 120
TGCCTGTCTG ACACAGACTG CAATACCAGA AAGTTCTGCC TCCAGTCCCA CAATGAGAAG 180
CCGTTCTGTG CTACATGTCG TGGGTTGCAG AGGAGGTGCC AGCGAGATGC CATGTGCTGC 240
CCTGGGACAC TCTGCATGAA TGATGTTTGT ACTACGATGG AAGACGCAAC CCCAAAATTG 300
GAAAGGCAGC TTGATGAGCA AGATGGCACA CATGCAGAAG TAACAACTGG GCACCCAGTC 360
CAGGAAAACC AACCCAAGAG GAAGCCAAGT ATTAAGAAAT CACAAGGCAG GAAGGGACAA 420
GAGGGAGAAA GTTGTCTGAG AACTTTTGAC TGTGGCCCTG GACTTTGCTG TGCTCGTCAT 480
TTTTGGACGA AAATTTGTAA GCCAGTCCTT TTGGAGGGAC AGGTCTGCTC CAGGAGAGGG 540
CATAAAGACA CTGCTCAAGC TCCAGAAATC TTCCAGCGTT GCGACTGTGG CCCCGGACTA 600
CTGTGTCGAA GCCAACTGAC CAGCAATCAG CAGCATGCAC GGTTACGAGT ATGCCAAAAA 660
ATAGAAAAGC TATAA 675

FIG. 1

1 MAAAVLLGLS WLCSPLGALV LDFNNIRSSA DLLGARKGSQ CLSDTDCNTR KFCLQSHNEK
61 PFCATCRGLQ RRCQRDAMCC PGTLCMNDVC TTMEDATPKL ERQLDEQDGT HAEVTTGHPV
121 QENQPKRKPS IKKSQGRKGQ EGESCLRTFD CGPGLCCARH FWTKICKPVL LEGQVCSRRG
181 HKDTAQAPEI FQRCDCGPGL LCRSQLTSNQ QHARLRVCQK IEKL

FIG. 2

```
                          1                                                  50
Human_Dkk-4(AF177397) GCACGAGAGA CGACGTGCTG AGCTGCCAGC TTAGTGGAAG CTCTGCTCTG
      Cyno_Dickkopf-4 .......... .......... .......... .......... ..........

                          51                                                100
Human_Dkk-4(AF177397) GGTGGAGAGC AGCCTCGCTT TGGTGACGCA CAGTGCTGGG ACCCTCCAGG
      Cyno_Dickkopf-4 .......... .......... .......... .......... ..........

                          101                                               150
Human_Dkk-4(AF177397) AGCCCCGGGA TTGAAGGATG GTGGCGGCCG TCCTGCTGGG GCTGAGCTGG
      Cyno_Dickkopf-4 .......... .......ATG GCGGCGGCCG TCCTGCTGGG ACTGAGCTGG

                          151                                               200
Human_Dkk-4(AF177397) CTCTGCTCTC CCCTGGGAGC TCTGGTCCTG GACTTCAACA ACATCAGGAG
      Cyno_Dickkopf-4 CTCTGCTCTC CCCTGGGAGC TCTGGTCCTG GACTTCAACA ACATCAGGAG

                          201                                               250
Human_Dkk-4(AF177397) CTCTGCTGAC CTGCATGGGG CCCGGAAGGG CTCACAGTGC CTGTCTGACA
      Cyno_Dickkopf-4 CTCTGCTGAC CTGCTTGGGG CCCGGAAGGG CTCACAGTGC CTGTCTGACA

                          251                                               300
Human_Dkk-4(AF177397) CGGACTGCAA TACCAGAAAG TTCTGCCTCC AGCCCCGCGA TGAGAAGCCG
      Cyno_Dickkopf-4 CAGACTGCAA TACCAGAAAG TTCTGCCTCC AGTCCCACAA TGAGAAGCCG

                          301                                               350
Human_Dkk-4(AF177397) TTCTGTGCTA CATGTCGTGG GTTGCGGAGG AGGTGCCAGC GAGATGCCAT
      Cyno_Dickkopf-4 TTCTGTGCTA CATGTCGTGG GTTGCAGAGG AGGTGCCAGC GAGATGCCAT

                          351                                               400
Human_Dkk-4(AF177397) GTGCTGCCCT GGGACACTCT GTGTGAACGA TGTTTGTACT ACGATGGAAG
      Cyno_Dickkopf-4 GTGCTGCCCT GGGACACTCT GCATGAATGA TGTTTGTACT ACGATGGAAG

                          401                                               450
Human_Dkk-4(AF177397) ATGCAACCCC AATATTAGAA AGGCAGCTTG ATGAGCAAGA TGGCACACAT
      Cyno_Dickkopf-4 ACGCAACCCC AAAATTGGAA AGGCAGCTTG ATGAGCAAGA TGGCACACAT

                          451                                               500
Human_Dkk-4(AF177397) GCAGAAGGAA CAACTGGGCA CCCAGTCCAG GAAAACCAAC CCAAAAGGAA
      Cyno_Dickkopf-4 GCAGAAGTAA CAACTGGGCA CCCAGTCCAG GAAAACCAAC CCAAGAGGAA
```

FIG.3A

```
                    501                                              550
Human_Dkk-4(AF177397) GCCAAGTATT AAGAAATCAC AAGGCAGGAA GGGACAAGAG GGAGAAAGTT
      Cyno_Dickkopf-4 GCCAAGTATT AAGAAATCAC AAGGCAGGAA GGGACAAGAG GGAGAAAGTT

                    551                                              600
Human_Dkk-4(AF177397) GTCTGAGAAC TTTTGACTGT GGCCCTGGAC TTTGCTGTGC TCGTCATTTT
      Cyno_Dickkopf-4 GTCTGAGAAC TTTTGACTGT GGCCCTGGAC TTTGCTGTGC TCGTCATTTT

                    601                                              650
Human_Dkk-4(AF177397) TGGACGAAAA TTTGTAAGCC AGTCCTTTTG GAGGGACAGG TCTGCTCCAG
      Cyno_Dickkopf-4 TGGACGAAAA TTTGTAAGCC AGTCCTTTTG GAGGGACAGG TCTGCTCCAG

                    651                                              700
Human_Dkk-4(AF177397) AAGAGGGCAT AAAGACACTG CTCAAGCTCC AGAAATCTTC CAGCGTTGCG
      Cyno_Dickkopf-4 GAGAGGGCAT AAAGACACTG CTCAAGCTCC AGAAATCTTC CAGCGTTGCG

                    701                                              750
Human_Dkk-4(AF177397) ACTGTGGCCC TGGACTACTG TGTCGAAGCC AATTGACCAG CAATCGGCAG
      Cyno-Dickkopf-4 ACTGTGGCCC CGGACTACTG TGTCGAAGCC AACTGACCAG CAATCAGCAG

                    751                                              800
Human_Dkk-4(AF177397) CATGCTCGAT TAAGAGTATG CCAAAAAATA GAAAAGCTAT AAATATTTCA
      Cyno_Dickkopf-4 CATGCACGGT TACGAGTATG CCAAAAAATA GAAAAGCTAT AA ........

                    801                                        841
Human_Dkk-4(AF177397) AAATAAAGAA GAATCCACAT TGCAAAAAAA AAAAAAAAAA A
      Cyno_Dickkopf-4 .......... ..........  .......... .......... .
```

FIG.3B

```
Cyno_Dickkopf-4 MAAAVLLGLS WLCSPLGALV LDFNNIRSSA DLLGARKGSQ CLSDTDCNTR
     Human_Dkk4 MVAAVLLGLS WLCSPLGALV LDFNNIRSSA DLHGARKGSQ CLSDTDCNTR
     Mouse_DKK4 MVLVTLLGLS WFCSPLAALV LDFNNIKSSA DVQGAGKGSL CASDRDCSEG

                51                                                   100
Cyno_Dickkopf-4 KFCLQSHNEK PFCATCRGLQ RRCQRDAMCC PGTLCMNDVC TTMEDATPKL
     Human_Dkk4 KFCLQPRDEK PFCATCRGLR RRCQRDAMCC PGTLCVNDVC TTMEDATPIL
     Mouse_DKK4 KFCLAFHDER SFCATCRRVR RRCQRSAVCC PGTVCVNDVC TAVEDTRPVM

                101                                                  150
Cyno_Dickkopf-4 ERQLDEQDGT HAEVTTGHPV QENQPKRKPS IKKSQGRKGQ EGESCLRTFD
     Human_Dkk4 ERQLDEQDGT HAEGTTGHPV QENQPKRKPS IKKSQGRKGQ EGESCLRTFD
     Mouse_DKK4 DRNTDGQDGA YAEGTTKWPA EENRPQGKPS TKKSQSSKGQ EGESCLRTSD

                151                                                  200
Cyno_Dickkopf-4 CGPGLCCARH FWTKICKPVL LEGQVCSRRG HKDTAQAPEI FQRCDCGPGL
     Human_Dkk4 CGPGLCCARH FWTKICKPVL LEGQVCSRRG HKDTAQAPEI FQRCDCGPGL
     Mouse_DKK4 CGPGLCCARH FWTKICKPVL REGQVCSRRG HKDTAQAPEI FQRCDCGPGL

                201                    224
Cyno_Dickkopf-4 LCRSQLTSNQ QHARLRVCQK IEKL
     Human_Dkk4 LCRSQLTSNR QHARLRVCQK IEKL
     Mouse_DKK4 TCRSQVTSNR QHSRLRVCQR I...
```

FIG.4

SEQUENCE LISTING

```
<160> NUMBER OF SEQ ID NOS: 13

<210> SEQ ID NO 1
<211> LENGTH: 675
<212> TYPE: DNA
<213> ORGANISM: MACACA FASCICULARIS

<400> SEQUENCE: 1

atggcggcgg ccgtcctgct gggactgagc tggctctgct ctcccctggg agctctggtc     60

ctggacttca acaacatcag gagctctgct gacctgcttg gggcccggaa gggctcacag    120

tgcctgtctg acacagactg caataccaga aagttctgcc tccagtccca caatgagaag    180

ccgttctgtg ctacatgtcg tgggttgcag aggaggtgcc agcgagatgc catgtgctgc    240

cctgggacac tctgcatgaa tgatgtttgt actacgatgg aagacgcaac ccccaaaattg   300

gaaaggcagc ttgatgagca agatggcaca catgcagaag taacaactgg gcacccagtc    360

caggaaaacc aacccaagag gaagccaagt attaagaaat cacaaggcag gaagggacaa    420

gagggagaaa gttgtctgag aacttttgac tgtggccctg gactttgctg tgctcgtcat    480
```

```
ttttggacga aaatttgtaa gccagtcctt ttggagggac aggtctgctc caggagaggg    540

cataaagaca ctgctcaagc tccagaaatc ttccagcgtt gcgactgtgg ccccggacta    600

ctgtgtcgaa gccaactgac cagcaatcag cagcatgcac ggttacgagt atgccaaaaa    660

atagaaaagc tataa                                                    675
```

<210> SEQ ID NO 2
<211> LENGTH: 224
<212> TYPE: PRT
<213> ORGANISM: MACACA FASCICULARIS

<400> SEQUENCE: 2

```
Met Ala Ala Ala Val Leu Leu Gly Leu Ser Trp Leu Cys Ser Pro Leu
 1               5                  10                  15

Gly Ala Leu Val Leu Asp Phe Asn Asn Ile Arg Ser Ser Ala Asp Leu
            20                  25                  30

Leu Gly Ala Arg Lys Gly Ser Gln Cys Leu Ser Asp Thr Asp Cys Asn
        35                  40                  45

Thr Arg Lys Phe Cys Leu Gln Ser His Asn Glu Lys Pro Phe Cys Ala
    50                  55                  60

Thr Cys Arg Gly Leu Gln Arg Arg Cys Gln Arg Asp Ala Met Cys Cys
65                  70                  75                  80

Pro Gly Thr Leu Cys Met Asn Asp Val Cys Thr Thr Met Glu Asp Ala
                85                  90                  95

Thr Pro Lys Leu Glu Arg Gln Leu Asp Glu Gln Asp Gly Thr His Ala
            100                 105                 110

Glu Val Thr Thr Gly His Pro Val Gln Glu Asn Gln Pro Lys Arg Lys
        115                 120                 125

Pro Ser Ile Lys Lys Ser Gln Gly Arg Lys Gly Gln Glu Gly Glu Ser
    130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
        195                 200                 205

Asn Gln Gln His Ala Arg Leu Arg Val Cys Gln Lys Ile Glu Lys Leu
    210                 215                 220
```

<210> SEQ ID NO 3
<211> LENGTH: 841
<212> TYPE: DNA
<213> ORGANISM: HOMO SAPIENS

<400> SEQUENCE: 3

```
gcacgagaga cgacgtgctg agctgccagc ttagtggaag ctctgctctg ggtggagagc     60

agcctcgctt tggtgacgca cagtgctggg accctccagg agccccggga ttgaaggatg    120

gtggcggccg tcctgctggg gctgagctgg ctctgctctc ccctgggagc tctggtcctg    180

gacttcaaca acatcaggag ctctgctgac ctgcatgggg cccggaaggg ctcacagtgc    240

ctgtctgaca cggactgcaa taccagaaag ttctgcctcc agccccgcga tgagaagccg    300

ttctgtgcta catgtcgtgg gttgcggagg aggtgccagc gagatgccat gtgctgccct    360
```

-continued

```
gggacactct gtgtgaacga tgtttgtact acgatggaag atgcaacccc aatattagaa    420

aggcagcttg atgagcaaga tggcacacat gcagaaggaa caactgggca cccagtccag    480

gaaaaccaac ccaaaaggaa gccaagtatt aagaaatcac aaggcaggaa gggacaagag    540

ggagaaagtt gtctgagaac ttttgactgt ggccctggac tttgctgtgc tcgtcatttt    600

tggacgaaaa tttgtaagcc agtccttttg gagggacagg tctgctccag aagagggcat    660

aaagacactg ctcaagctcc agaaatcttc cagcgttgcg actgtggccc tggactactg    720

tgtcgaagcc aattgaccag caatcggcag catgctcgat taagagtatg ccaaaaaata    780

gaaaagctat aaatatttca aaataaagaa gaatccacat tgcaaaaaaa aaaaaaaaaa    840

a                                                                    841
```

<210> SEQ ID NO 4
<211> LENGTH: 224
<212> TYPE: PRT
<213> ORGANISM: HOMO SAPIENS

<400> SEQUENCE: 4

```
Met Val Ala Ala Val Leu Leu Gly Leu Ser Trp Leu Cys Ser Pro Leu
 1               5                  10                  15

Gly Ala Leu Val Leu Asp Phe Asn Asn Ile Arg Ser Ser Ala Asp Leu
            20                  25                  30

His Gly Ala Arg Lys Gly Ser Gln Cys Leu Ser Asp Thr Asp Cys Asn
        35                  40                  45

Thr Arg Lys Phe Cys Leu Gln Pro Arg Asp Glu Lys Pro Phe Cys Ala
    50                  55                  60

Thr Cys Arg Gly Leu Arg Arg Arg Cys Gln Arg Asp Ala Met Cys Cys
65                  70                  75                  80

Pro Gly Thr Leu Cys Val Asn Asp Val Cys Thr Thr Met Glu Asp Ala
                85                  90                  95

Thr Pro Ile Leu Glu Arg Gln Leu Asp Glu Gln Asp Gly Thr His Ala
            100                 105                 110

Glu Gly Thr Thr Gly His Pro Val Gln Glu Asn Gln Pro Lys Arg Lys
        115                 120                 125

Pro Ser Ile Lys Lys Ser Gln Gly Arg Lys Gly Gln Glu Gly Glu Ser
    130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
        195                 200                 205

Asn Arg Gln His Ala Arg Leu Arg Val Cys Gln Lys Ile Glu Lys Leu
    210                 215                 220
```

<210> SEQ ID NO 5
<211> LENGTH: 221
<212> TYPE: PRT
<213> ORGANISM: MUS MUSCULUS

<400> SEQUENCE: 5

```
Met Val Leu Val Thr Leu Leu Gly Leu Ser Trp Phe Cys Ser Pro Leu
 1               5                  10                  15
```

-continued

```
Ala Ala Leu Val Leu Asp Phe Asn Asn Ile Lys Ser Ser Ala Asp Val
            20                  25                  30

Gln Gly Ala Gly Lys Gly Ser Leu Cys Ala Ser Asp Arg Asp Cys Ser
        35                  40                  45

Glu Gly Lys Phe Cys Leu Ala Phe His Asp Glu Arg Ser Phe Cys Ala
    50                  55                  60

Thr Cys Arg Arg Val Arg Arg Arg Cys Gln Arg Ser Ala Val Cys Cys
65                  70                  75                  80

Pro Gly Thr Val Cys Val Asn Asp Val Cys Thr Ala Val Glu Asp Thr
                85                  90                  95

Arg Pro Val Met Asp Arg Asn Thr Asp Gly Gln Asp Gly Ala Tyr Ala
            100                 105                 110

Glu Gly Thr Thr Lys Trp Pro Ala Glu Glu Asn Arg Pro Gln Gly Lys
        115                 120                 125

Pro Ser Thr Lys Lys Ser Gln Ser Ser Lys Gly Gln Glu Gly Glu Ser
    130                 135                 140

Cys Leu Arg Thr Ser Asp Cys Gly Pro Gly Leu Cys Cys Ala Arg His
145                 150                 155                 160

Phe Trp Thr Lys Ile Cys Lys Pro Val Leu Arg Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Thr Cys Arg Ser Gln Val Thr Ser
        195                 200                 205

Asn Arg Gln His Ser Arg Leu Arg Val Cys Gln Arg Ile
    210                 215                 220
```

```
<210> SEQ ID NO 6
<211> LENGTH: 24
<212> TYPE: DNA
<213> ORGANISM: Artificial Sequence
<220> FEATURE:
<223> OTHER INFORMATION: F2 PRIMER

<400> SEQUENCE: 6

caggagcccc gggattgaag gatg                                            24


<210> SEQ ID NO 7
<211> LENGTH: 38
<212> TYPE: DNA
<213> ORGANISM: Artificial Sequence
<220> FEATURE:
<223> OTHER INFORMATION: R2 PRIMER

<400> SEQUENCE: 7

gcaatgtgga ttcttcttta ttttgaaata tttatagc                             38


<210> SEQ ID NO 8
<211> LENGTH: 31
<212> TYPE: DNA
<213> ORGANISM: Artificial Sequence
<220> FEATURE:
<223> OTHER INFORMATION: F PRIMER

<400> SEQUENCE: 8

gcgaattcac catggcggcg gccgtcctgc t                                    31


<210> SEQ ID NO 9
<211> LENGTH: 37
<212> TYPE: DNA
```

-continued

```
<213> ORGANISM: Artificial Sequence
<220> FEATURE:
<223> OTHER INFORMATION: FF PRIMER

<400> SEQUENCE: 9

gcgaattcac catggcggcg gccgtcctgc tgggact                              37


<210> SEQ ID NO 10
<211> LENGTH: 42
<212> TYPE: DNA
<213> ORGANISM: Artificial Sequence
<220> FEATURE:
<223> OTHER INFORMATION: R PRIMER

<400> SEQUENCE: 10

gcgaattcta gcttttctat tttttggcat actcgtaacc gt                        42


<210> SEQ ID NO 11
<211> LENGTH: 47
<212> TYPE: DNA
<213> ORGANISM: Artificial Sequence
<220> FEATURE:
<223> OTHER INFORMATION: RR PRIMER

<400> SEQUENCE: 11

gcgaattcta gcttttctat tttttggcat actcgtaacc gtgcatg                   47


<210> SEQ ID NO 12
<211> LENGTH: 22
<212> TYPE: DNA
<213> ORGANISM: Artificial Sequence
<220> FEATURE:
<223> OTHER INFORMATION: Fseq PRIMER

<400> SEQUENCE: 12

gggacactct gcatgaatga tg                                              22


<210> SEQ ID NO 13
<211> LENGTH: 21
<212> TYPE: DNA
<213> ORGANISM: Artificial Sequence
<220> FEATURE:
<223> OTHER INFORMATION: Rseq PRIMER

<400> SEQUENCE: 13

tgccatcttg ctcatcaagc t                                               21
```

CYNOMOLGUS MONKEY DICKKOPF-4, NUCLEOTIDES ENCODING SAME, AND USES THEREOF

CROSS REFERENCE TO RELATED APPLICATIONS

This patent application claims benefit of International Patent Application No. PCT/US20041037799, which was filed 12 Nov. 2004, and U.S. Provisional application No. 60/520,569, which was filed 17 Nov. 2003.

BACKGROUND OF THE INVENTION (1) Field of the Invention

The present invention relates to treatments for osteoporosis and other disorders characterized by bone loss or insufficient bone mass. More specifically, the present invention relates to the cynomolgus monkey Dickkopf-4 (cDkk-4) protein, to isolated nucleic acid molecules which encode the cDkk-4 protein, and to recombinant vectors and hosts comprising DNA encoding the cDkk-4 protein. The present invention further relates to methods for identifying analytes which interfere with the interaction between the cDkk-4 protein and a homologous or heterologous Dkk receptor and analytes which interfere with the interaction and stimulate bone formation. Analytes identified using one or more of the methods are useful for treating osteoporosis and other bone loss disorders.

(2) Description of Related Art

The skeletal disorder osteoporosis is the leading cause of morbidity in the elderly. Osteoporosis is characterized by bone loss resulting from an imbalance between bone resorption (destruction) and bone formation. This condition leads to an increased risk of bone fractures, which may occur following low levels of trauma. In the United States, there are currently about 20 million people with detectable fractures of the vertebrae due to osteoporosis. Mortality due to bone fractures is not uncommon among the elderly patient population Elderly, post-menopausal women are at the highest risk of developing osteoporosis due to a deficiency of estrogen, which is necessary for proper bone maintenance. Insufficient estrogen levels lead to increased production and longevity of destructive osteoclasts, which in turn, leads to increased bone resorption. As a result, an average of 5% bone loss is observed in the vertebrae per year. Although less common, osteoporosis also affects elderly men. The existence of osteoporosis in elderly men may also be due, in part, to insufficient estrogen levels caused by a decrease in circulating testosterone.

Therapeutic strategies for overcoming bone loss include both the prevention of bone resorption and the stimulation of bone growth. The majority of therapeutic targets that have led to efficacious osteoporosis treatments fall into the former category. Thus, the first line of treatment/prevention of this condition has historically been the inhibition of bone resorption using compounds such as bisphosphonates, estrogens, selective estrogen receptor modulators (SERMs), and calcitonin. Because inhibition of bone resorption cannot restore bone mass, this approach is an ineffective treatment for patients who have already lost a significant amount of bone (>30%). Additionally, the effectiveness of osteoporosis treatments that function by this mechanism is not consistent across the skeletal anatomy because the rate of bone turnover differs from one site to another. For example, the bone turnover rate is higher in the trabecular bone of the vertebrae than in the cortex of the long bones; thus, bone resorption inhibitors are less effective in increasing hip bone mineral density (BMD) and preventing hip fracture. Therefore, osteoanabolic agents, which increase cortical/periosteal bone formation and bone mass at long bones, would address an unmet need in the treatment of osteoporosis, especially for patients with high risk of hip fractures.

One potential therapeutic target for metabolic disorders, including osteoporosis, is the low-density lipoprotein receptor related protein 5 (LRP5). LRP5 belongs to the low density lipoprotein receptor (LDLR) gene family of cell surface receptors, characterized by cysteine-rich, complement-type LDLR ligand binding domains. LRP5 was isolated based on its proximity to the locus of osteoporosis pseudoglioma syndrome (OPG), an autosomal recessive disorder characterized by severe osteoporosis (Hey et al., Gene 216: 103-111 (1998); Todd et al., WO 98/46743). Additional support for the notion that LRP5 represents a therapeutic target for osteoporosis comes from the observation that loss-of-function mutations of LRP5 lead to OPG (Gong et al., Cell 107: 513-523 (2001)).

Interestingly, aberrant expression of LRP5 is also associated with high bone mass trait (HBM), an autosomal dominant human genetic skeletal condition characterized by strilingly increased bone mass. Positional cloning of the HBM mutation demonstrated that HBM results from a G171V mutation of the LRP5 gene that leads to a gain of function (Little et al., Am. J. Hum. Genet. 70: 11-19 (2002); Boyden et al., N. Eng. J. Med. 346: 1513-1521 (2002)). These complementary findings, together with the finding that null mutations of LRP5 in mice results in severe bone loss (Kato, J. Cell Biol. 157: 303-314 (2002)), suggest that LRP5 has an important role in bone formation and bone mass in humans.

Despite its specific role in stimulating bone growth, the LRP5 gene was shown to have a nearly ubiquitous expression profile. The mechanism by which activation of LRP5 leads to osteogenesis is not known. However, at the molecular level, it was recently shown that LRP5 and closely related LRP6 are involved in Wingless (Wnt) signaling as co-receptors for Wnt. Wnt activated genes encode secreted proteins implicated in a diverse array of developmental and adult physiological processes, such as mediating cell growth and differentiation in the central nervous system. It was also shown that LRP5 and LRP6 are receptors for the secreted protein Dickkopf-1 (Dkk-1) and that their association with Dkk-1 represses Wnt signaling (Mao et al., Nature 411: 321-325 (2001); Semenov et al., Curr. Biol. 11: 951-961 (2001); Bafico et al., Nat. Cell Biol. 3: 683-686 (2001)).

Dickkopf-1 is a secreted protein that participates in embryonic head induction and antagonizes Wnt signaling (Glinka et al., Nature 391: 357-362 (1998)). The amino acid sequence of human Dkk-1 protein and the nucleotides encoding it have been described in WO 00/52047 to McCarthy and Krupnick et al., Gene 238: 301-313(1999). Expression of Dkk-1 in humans was thought to be restricted to the placenta, suggesting a role for Dkk-1 in embryonic development (Krupnick et al., supra). WO 02/092015 to Allen et al. describes assays relating to the interaction between LRP5, HBM (a variant of LRP5), or LRP6 with Dkk-1. In humans, Dickkopf-1 is a member of a Dickkopf gene family which at present has been shown to include Dkk-1, Dkk-2, Dkk-3, and Dkk-4 (Krupnick et al., supra). While Dkk-1 and Dkk-4, but not Dkk-2 or Dkk-3, have been shown to suppress Wnt-induced secondary axis induction in *Xenopus* embryos, neither block axis induction triggered either by *Xenopus* Dishevelled protein or Frizzled protein which suggests that their Wnt inhibitory activity is by a mechanism upstream of the Frizzled protein's position in the Wnt signaling pathway (Krupnick et al., supra). It has been suggested that Dkk-1 or Dkk-2 might have an inhibitory effect on bone formation and that either might be a target for the prevention or treatment of osteoporosis (Patel and Karensky, N. Eng. J. Med. 346: 1572-1573 (2002); Boyden et al., N. Eng. J. Med. 346: 1513-1521 (2002)). A role for Dkk-4 in the Wnt signaling pathway is not clear.

In addition to LRP5 and LRP6, recent studies indicate that the transmembrane proteins kremen1 and kremen2 are high-affinity Dkk-1 receptors which functionally cooperate with Dkk-1 to block Wnt signaling, thereby regulating central nervous system patterning during embryonic development (Mao et al., Nature 417: 664-667 (2002); Davidson et al., Development 129: 5587-96 (2002)). Currently, it is believed that Dkk-1 inhibits LRP5 or LRP6 activated Wnt signaling by cooperating with kremen to form a ternary complex with the LRP5 or LRP6. The ternary complex is rapidly endocytosed which removes the LPR5 or LRP6 from the membrane, thus preventing LPR5 or LPR6 from binding Wnt.

Despite our increased understanding of the regulation of bone formation, osteoporosis has remained a leading health concern because traditional therapies, which act by preventing bone loss, are ineffective treatments for patients who have already suffered significant bone loss. Because patients who have lost significant bone tissue have bones which are brittle and easily broken, it would be particularly desirable to have treatments for osteoporosis (and other disorders characterized by bone-loss) which are osteoanabolic, that is, treatments which stimulate bone growth. Therefore, there is a need for a method for identifying compounds or drugs for treating osteoporosis and other bone mass disorders which stimulate bone growth. Such compounds would be an ideal treatment for osteoporosis as a monotherapy or in combination with inhibitors of bone resorption, such as bisphosphonates, estrogens, SERMs, cathepsin K inhibitors, $\alpha V\beta 3$ antagonists, calcitonin, proton pump inhibitors.

BRIEF SUMMARY OF THE INVENTION

The present invention provides methods for identifying analytes which interfere with the interaction between the *Macaca fascicularis* (cynomolgus monkey) Dickkopf-4 (cDkk-4) protein and a homologous or heterologous Dkk receptor or binding partner. In one aspect, the present invention provides an isolated cDkk-4 protein, isolated nucleic acid molecules which encode the cDkk-4 protein, and recombinant vectors and hosts comprising the nucleic acid encoding the cDkk-4 protein. In another aspect, the present invention provides methods for using the isolated cDkk-4 protein to identify analytes which interfere with the interaction between the cDkk-4 protein and one or more homologous or heterologous Dkk receptors or binding partners such as human LRP5, LRP6, kremen1, or kremen2 and which stimulate bone formation. Analytes identified using one or more of the methods disclosed herein are useful for treating osteoporosis and other bone mass disorders characterized by bone loss.

Therefore, the present invention provides an isolated nucleic acid molecule comprising a nucleotide sequence encoding a cDkk-4 protein which has an amino acid sequence as set forth in SEQ ID NO:2. In further embodiments, the isolated nucleic acid is a DNA molecule, an RNA molecule, or a cDNA molecule. In a further-still embodiment, the nucleic acid has a nucleotide sequence substantially as set forth in SEQ ID NO:1. The present invention further provides a protein comprising an amino acid sequence as set forth in SEQ ID NO:2. It is preferable that the cDkk-4 protein be capable of binding a Dkk receptor, preferably, a Dkk receptor selected from the group consisting of low-density lipoprotein receptor protein 5 (LRP5), low-density lipoprotein receptor protein 6 (LRP6), kremen1, and kremen2. It is particularly preferable that the cDkk-4 be capable of binding LRP5 or LRP6.

The present invention further provides an antibody which binds a protein comprising an amino acid sequence as set forth in SEQ ID NO:2. In particular embodiments, the antibody is selected from the group consisting of polyclonal antibodies, monoclonal antibodies, single VH chain antibodies, Fab fragments, and recombinant antibodies. In embodiments in which the antibody is a recombinant antibody, the recombinant antibody includes recombinant antibodies selected from the group consisting of scFv polypeptides and VH chain polypeptides.

The present invention further provides a vector comprising a nucleic acid encoding a cDkk-4 protein which has an amino acid sequence as set forth in SEQ ID NO:2. In particular embodiments, the vector is selected from the group consisting of plasmids and viruses. In further still embodiments, the nucleic acid is operably linked to a promoter which includes one or more regulatory sequences which enable expression of the polypeptide. In particular embodiments, the promoter provides inducible expression and in other embodiments, the promoter provides constitutive expression. In a further still embodiment, the nucleic acid includes the nucleotide sequence set forth in SEQ ID NO:1.

The present invention further provides a cell comprising a nucleic acid encoding a cDkk-4 protein which has an amino acid sequence as set forth in SEQ ID NO:2 wherein the nucleic acid is operably linked to a heterologous promoter. The cell can be a prokaryote cell or a eukaryote cell. In embodiments which include eukaryote cells, the cell can be of mammalian, insect, amphibian, fungal, or plant origin.

The present invention further provides a method for producing a cDkk4 protein which binds a homologous or heterologous low-density lipoprotein receptor protein 5 (LRP5) comprising (a) providing a nucleic acid encoding the cDkk-4 protein operably linked to a heterologous promoter; (b) introducing the nucleic acid into a cell to produce a recombinant cell; and (c) culturing the recombinant cell under conditions which allows expression of the cDkk-4 protein to produce the cDkk-4. In further embodiments, the nucleic acid encodes a protein which comprises an amino acid sequence as set forth in SEQ ID NO:2 or the nucleic acid has a nucleotide sequence as set forth in SEQ ID NO:1. In some embodiments, the cell is a prokaryote cell and in other embodiments, the cell is a eukaryote cell. In further embodiments, the LRP5 is a human LRP5.

The present invention further provides a method for determining whether an analyte is an antagonist of Dickkopf 4 (Dkk-4) comprising providing a polypeptide comprising the extracellular domain of a Dkk-4 receptor; contacting the polypeptide with a cynomolgus monkey Dkk-4 (cDkk-4) and the analyte; and determining whether binding of the cDkk-4 to the polypeptide is decreased in the presence of the analyte, wherein a decrease in the binding indicates that the analyte is an cDkk-4 antagonist.

In a further aspect of the above method, the Dkk-4 receptor is low-density lipoprotein receptor related protein 5 (LRP5) or low density lipoprotein receptor related protein 6 (LRP6) or the receptor is kremen1 or kremen2.

In further still aspects, the cDkk-4 is labeled with a detectable molecule, for example, alkaline phosphatase, radioactive isotope, lanthanide such as europium, or a fluorescent dye, or the cDkk-4 is a fusion protein in which the amino or carboxyl terminus of the cDkk-4 is covalently linked to a detectable protein or polypeptide, including but not limited to, c-myc, which can be detected using an antibody against the c-myc, or an enzyme, for example, alkaline phosphatase, which can be detected in a colorimetric assay, or other detectable protein, for example, luciferase or Green fluorescent protein, which can detected by monitoring emission of light or fluorescence.

The present invention further provides a method for determining whether an analyte is an antagonist of Dickkopf-4 (Dkk-4) protein, which comprises providing a recombinant cell which produces one or more Dkk-4 receptors; introducing a reporter expression vector into the recombinant cell which comprises a reporter gene operably linked to a promoter responsive to Wnt-mediated signal transduction to provide a second recombinant cell; exposing the second recombinant cell to the analyte and to a cynomolgus monkey Dkk-4 (cDkk-4); and measuring expression of the reporter gene, wherein an increase in expression of the reporter gene in the presence of the analyte relative to expression of the reporter gene in the absence of the analyte indicates that the analyte is a Dkk-4 antagonist.

In further aspects of the above method, the one or more Dkk-4 receptors are selected from the group consisting of low-density lipoprotein receptor protein 5 (LRP5), low-density lipoprotein receptor protein 6 (RP6), kremen1, kremen2, and combinations thereof.

In particular aspects, the reporter gene is selected from the group consisting of the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites. In further still aspects of the above method, the promoter comprises one or more lymphoid enhancer factor/T cell factor (TCF/LEF) binding sites.

In further still aspects of the above method, the cDkk-4 is provided exogenously as an isolated cDkk-4 protein or as a component of a medium obtained from a culture comprising a second recombinant cell which expresses the cDkk-4 or the cDkk-4 is provided by cotransfecting the second recombinant cell with an expression vector encoding the cDkk-4.

In further still aspects of the above method, a Wnt ligand is provided exogenously to the second recombinant cell as an isolated Wnt ligand or as a component of a medium obtained from a culture comprising a second recombinant cell which expresses the Wnt ligand or the Wnt ligand is provided to the second recombinant cell by cotransfecting the second recombinant cell with an expression vector encoding the Wnt ligand.

The present invention further provides a method for determining whether an analyte interferes with binding of Dickkopf-4 (Dkk-4) protein to a Dkk-4 receptor, which comprises providing a recombinant cell which expresses the Dkk-4 receptor; culturing the recombinant cell in a culture medium which contains a cynomolgus monkey Dkk-4 (cDkk-4) protein and the analyte; and measuring the cDkk-4 bound to the cDkk-4 receptor, wherein a decrease in the cDkk-4 protein bound to the Dkk-4 receptor in the presence of the analyte relative to cDkk-4 protein bound in the absence of the analyte indicates that the analyte interferes with the binding of the Dkk-4 protein to the Dkk-4 receptor.

In further aspects of the above method, the Dkk-4 receptor is selected from the group consisting of low-density lipoprotein receptor protein 5 (LRP5), low-density lipoprotein receptor protein 6 (LRP6), kremen1, kremen2, and combinations thereof.

In further still aspects, the cDkk-4 is labeled with a detectable molecule, for example, alkaline phosphatase, radioactive isotope, lanthanide such as europium, or a fluorescent dye, or the cDkk-4 is a fusion protein in which the amino or carboxyl terminus of the cDkk-4 is covalently linked to a detectable protein or polypeptide, including but not limited to, c-myc, which can be detected using an antibody against the c-myc, or an enzyme, for example, alkaline phosphatase, which can be detected in a colorimetric assay, or other detectable protein, for example, luciferase or Green fluorescent protein, which can detected by monitoring emission of light or fluorescence.

The present invention further provides a method of identifying an analyte that induces Wnt signaling comprising: transfecting a recombinant cell expressing one or more Dkk-4 receptors with a reporter gene operably linked to a promoter responsive to Wnt-mediated signal transduction; exposing the cells to an analyte, cynomolgus monkey Dkk-4 (cDkk-4), and a Wnt ligand; measuring expression of the reporter gene, wherein an increase in expression of the reporter gene in the presence of the analyte relative to expression of the reporter gene in the absence of the analyte indicates that the analyte induces the Wnt signaling.

In further aspects of the above methods, the one or more Dkk-4 receptors are selected from the group consisting of low-density lipoprotein receptor protein 5 (LRPS), low-density lipoprotein receptor protein 6 (LRP6), kremen1, kremen2, and combinations thereof.

In particular aspects, the reporter gene is selected from the group consisting of the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites. In further still aspects of the above method, the promoter comprises one or more lymphoid enhancer factor/T cell factor (TCF/LEF) binding sites.

In further still aspects of the above method, the cDkk-4 is provided exogenously as an isolated cDkk-4 protein or as a component of a medium obtained from a culture comprising a second recombinant cell which expresses the cDkk-4 or the cDkk-4 is provided by cotransfecting the second recombinant cell with an expression vector encoding the cDkk-4.

In further still aspects of the above method, a Wnt ligand is provided exogenously to the second recombinant cell as an isolated Wnt ligand or as a component of a medium obtained from a culture comprising a second recombinant cell which expresses the Wnt ligand or the Wnt ligand is provided to the second recombinant cell by cotransfecting the second recombinant cell with an expression vector encoding the Wnt ligand.

The present invention further provides a method for determining whether a compound inhibits Dickkopf 4 (Dkk-4) protein suppression of osteoblast differentiation comprising providing pluripotent cells which can be induced to differentiate along an osteoblast lineage; transfecting the cells with a first expression vector which expresses a cynomolgus monkey Dkk-4 (cDkk-4) protein, a second expression vector, which expresses low-density lipoprotein receptor protein (RP), and a third expression vector which expresses Wnt protein; incubating the cells in a medium containing the analyte for a time sufficient for expression of the cDkk-4 protein, LRP, and Wnt protein; and measuring expression of one or more osteoblastic markers wherein expression of the one or more markers indicates that the analyte inhibits cDkk-4 suppression of osteoblast differentiation.

In further aspects of the above methods, the pluripotent cell is a pluripotent marrow stromal cell or a pluripotent mesenchymal cell. In a further still embodiment, the pluripotent cell is selected from the group consisting of ST2 cells and C3H10T1/2 cells. In further still embodiments, the LRP is selected from the group consisting of LRP5 or LRP6. In a further still embodiment, the one or more osteoblastic markers are selected from the group consisting of alkaline phosphatase, Bglap, and Runx2. Preferably, the osteoblastic marker is alkaline phosphatase activity. In further embodiments, the LRP5 and Wnt protein are heterologous and in further still embodiments, the LRP5 and Wnt protein are of human origin.

As used throughout the specification and in the appended claims, the singular forms "a," "an," and "the" include the plural reference unless the context clearly dictates otherwise.

As used throughout the specification and appended claims, the following definitions and abbreviations apply.

The term "cDkk-4 protein" means that the cDkk-4 protein is of cynomolgus monkey origin, either isolated from cynomolgus monkey tissue, produced from a nucleic acid obtained from the cynomolgus monkey by recombinant means, produced from a nucleic acid synthesized in vitro but which encodes the cDkk-4 protein, or synthesized in vitro. The term further includes biologically active fragments or portions of the cDkk-4 protein.

The term "Dkk-4 protein" means that the Dkk-4 protein is not of cynomolgus monkey origin. The Dkk-4 protein can be from another organism, for example, insects such as *Drosophila,* amphibians such as *Xenopus,* mammals such as rat and mouse, and humans. The Dkk-4 protein can either be isolated from tissue of the organism, produced from a nucleic acid obtained from the organism by recombinant means, produced from a nucleic acid synthesized in vitro but which encodes the Dkk-4 protein, or synthesized in vitro. The term further includes biologically active fragments or portions of the Dkk-4 protein.

The term "Dkk protein" means that the protein is selected from the group consisting of Dkk-1 protein, Dkk-2 protein, Dkk-3 protein, and Dkk-4 protein. The Dkk protein can be of cynomolgus monkey origin or originate from another organism, for example, insects such as *Drosophila,* amphibians such as *Xenopus,* mammals such as rat and mouse, and humans. The Dkk protein can either be isolated from tissue of the cynomolgus monkey or organism or produced from a nucleic acid obtained from the cynomolgus monkey or organism by recombinant means, produced from a nucleic acid synthesized in vitro but which encodes the Dkk protein, or synthesized in vitro. The term further includes biologically active fragments or portions of the Dkk protein.

The term "Dkk receptor" means a binding partner of Dkk-4 which binds or interacts with the cDkk-4 protein or Dkk-4 protein. The term further includes binding partners which can bind one or more Dkk proteins selected from the group consisting of Dkk-1 protein, Dkk-2 protein, Dkk-3 protein, and Dkk-4 protein regardless of whether they originate from the cynomolgus monkey, another organism, expressed from a nucleic acid synthesized in vitro, or synthesized in vitro. Examples of binding partners include LRP5, LRP6, kremen1, and kremen2. The term further includes biologically active fragments or portions of the binding partner.

The term "homologous Dkk receptor" means a Dkk receptor of cynomolgus monkey origin. In other words, the Dkk receptor is isolated from the cynomolgus monkey or obtained from recombinant cells expressing the receptor from DNA encoding the cynomolgus monkey receptor. The homologous Dkk receptor can be a receptor specific for cDkk-4 protein or Dkk-4 protein or a receptor which can bind one or more of Dkk-1 protein, Dkk-2 protein, Dkk-3 protein, or Dkk-4 protein.

The term "heterologous Dkk receptor" means a Dkk receptor not of cynomolgus monkey origin. For example, the Dkk receptor is isolated from a human or obtained from recombinant cells expressing the receptor from DNA encoding the human receptor. The heterologous Dkk receptor can be a receptor specific for cDkk-4 protein or Dkk-4 protein or a receptor which can bind one or more of Dkk-1 protein, Dkk-2 protein, Dkk-3 protein, or Dkk-4 protein.

The term "promoter" refers to a recognition site on a DNA strand to which RNA polymerase binds. The promoter forms an initiation complex with RNA polymerase to initiate and drive transcriptional activity of a nucleic acid sequence located downstream from the promoter. The promoter can be modified by including activating sequences termed "enhancers" or inhibiting sequences termed "silencers" within the promoter. The term further includes both promoters which are inducible and promoters which are constitutive.

The term "cassette" refers to a nucleotide or gene sequence that is to be expressed from a vector, for example, the nucleotide or gene sequence encoding the cDkk-4 protein. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The term "vector" refers to a means by which DNA fragments can be introduced into a host organism or host tissue. There are various types of vectors including plasmid, virus (including adenovirus), bacteriophage, and cosmid.

"Substantially free from other nucleic acids" means at least 90%, preferably 95%, more preferably 99%, and even more preferably 99.9%, free of other nucleic acids. As used interchangeably, the terms "substantially free from other nucleic acids," "substantially purified," "isolated nucleic acid" or "purified nucleic acid" also refer to DNA molecules which comprise a coding region for a cDkk-4 polypeptide that has been purified away from other cellular components. Thus, a cDkk-4 DNA preparation that is substantially free from other nucleic acids will contain, as a percent of its total nucleic acid, no more than 10%, preferably no more than 5%, more preferably no more than 1%, and even more preferably no more than 0.1%, of non-cDkk-4 nucleic acids. Whether a given cDkk-4 DNA preparation is substantially free from other nucleic acids can be determined by such conventional techniques of assessing nucleic acid purity such as agarose gel electrophoresis combined with an appropriate staining method such as ethidium bromide staining, or by sequencing.

"Substantially free from other polypeptides" or "substantially purified" means at least 90%, preferably 95%, more preferably 99%, and even more preferably 99.9%, free of other proteins. Thus, a cDkk-4 protein preparation that is substantially free from other proteins will contain, as a percent of its total protein, no more than 10%, preferably no more than 5%, more preferably no more than 1%, and even more preferably no more than 0.1%, of non-cDkk-4 proteins. Whether a given cDkk-4 protein preparation is substantially free from other proteins can be determined by such conventional techniques of assessing protein. purity as, e.g., sodium dodecyl sulfate polyacrylamide gel electrophoresis (SDS- PAGE) combined with appropriate detection methods, for example, silver staining or immunoblotting.

As used interchangeably, the terms “substantially free from other proteins” or “substantially purified,” or “isolated cDkk-4 protein” or “purified cDkk-4 protein” also refer to cDkk-4 protein which has been isolated from a natural source. Use of the term “isolated” or “purified” indicates that cDkk-4 protein has been removed from its normal cellular environment. Thus, an isolated cDkk-4 protein may be in a cell-free solution or placed in a different cellular environment from that in which it occurs naturally. The term isolated does not imply that an isolated cDkk-4 protein is the only-protein present, but instead means that an cDkk-4 protein is substantially free of other proteins and non-amino acid material (for example, nucleic acids, lipids, carbohydrates) naturally associated with the cDkk-4 protein in vivo. Thus, a cDkk-4 protein that is recombinantly expressed in a prokaryotic or eukaryotic cell and substantially purified from this host cell and which does not naturally (that is, without intervention) express this cDkk-4 protein is an “isolated cDkk-4 protein” under any of circumstances referred to herein. As noted above, a cDkk-4 protein preparation that is an isolated or purified cDkk-4 protein will be substantially free from other proteins and will contain, as a percent of its total protein, no more than 10%, preferably no more than 5%, more preferably no more than 1%, and even more preferably no more than 0.1%, of non-cDkk-4 protein.

A “conservative amino acid substitution” refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term “mammalian” refers to any mammal, including a human being.

The term “treatment” refers to both therapeutic treatment and prophylactic or preventative measures. Those in need of treatment include those already with the disorder as well as those prone to have the disorder or those in which the disorder is to be prevented.

A “disorder” is any condition that would benefit from treatment with molecules identified by the methods described herein. This includes chronic and acute disorders or diseases including those pathological conditions which predispose the mammal to the disorder in question. The methods of the present invention are intended to identify molecules to be used for the treatment of disorders or conditions associated with aberrant bone mass, including, but not limited to, osteoporosis, bone fractures, osteomyelitis, hypercalcemia, osteogenesis imperfecta, and anorexia. Also contemplated is the use of the methods described herein to identify molecules for the treatment of disorders of cholesterol, glucose, and/or fat metabolism such as diabetes mellitus, hypercholesterolemia, or obesity.

The term “analyte” includes molecule, compound, composition, drug, protein, peptide, nucleic acid, antibody and active fragment thereof, nucleic acid aptamer, peptide aptamer, and the like.

BRIEF DESCRIPTION OF THE DRAWINGS

FIG. 1 shows the nucleotide sequence encoding the cynomolgus monkey cDkk-4 protein (SEQ ID NO:1). The position of various restriction endonuclease sites are shown.

FIG. 2 shows the amino acid sequence for the cynomolgus monkey cDkk-4 protein.

FIG. 3 shows the nucleotide sequence encoding the cynomolgus monkey cDkk-4 protein (SEQ ID NO:1) aligned with the nucleotide sequence encoding the human Dkk-4 protein (SEQ ID NO:3).

FIG. 4 shows the amino acid sequence of the cynomolgus monkey cDkk-4 protein (SEQ ID NO:2) aligned with the amino acid sequences for the human Dkk-4 protein (SEQ ID NO:4) and the mouse Dkk-4 protein (SEQ ID NO:5).

DETAILED DESCRIPTION OF THE INVENTION

Figure 5:
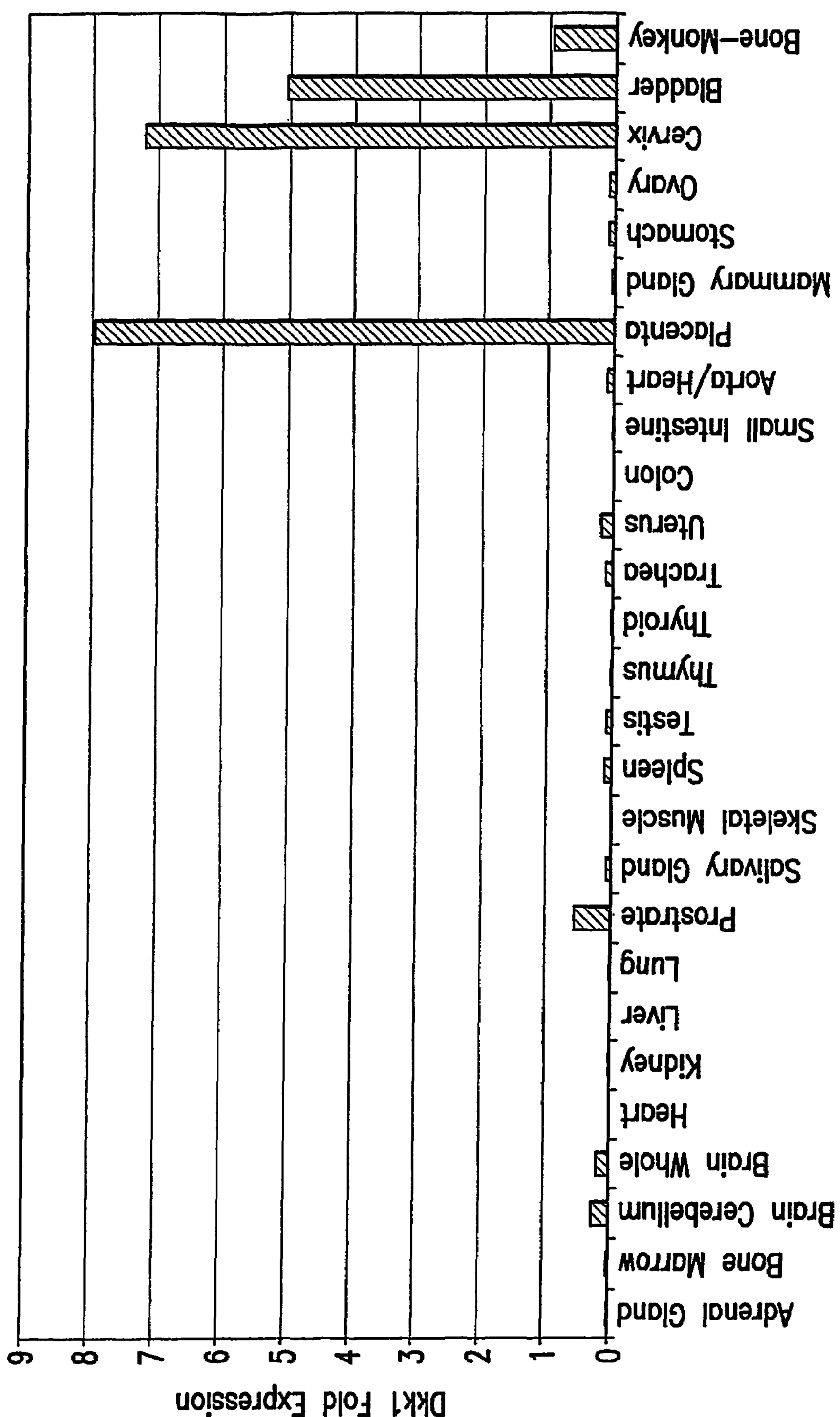
FIG. 5 shows a bar graph of Dkk-1 gene expression in a variety of human tissues compared to Dkk-1 expression in monkey bone. Expression was measured by TAQMAN RT-PCR analysis of cDNA prepared from RNA isolated from the tissue.

Osteoporosis is characterized by bone loss resulting from an imbalance between bone resorption (destruction) and bone formation. This skeletal disorder often leads to morbidity and mortality among the elderly, due in part to insufficient estrogen levels. Finding novel treatments for osteoporosis is a leading health concern because traditional therapies, which act by preventing bone loss, are ineffective treatments for patients who have already suffered significant bone loss. Therefore, a method which can identify analytes that stimulate bone growth, particularly in patients who have suffered significant bone loss, would be an invaluable tool for discovering and designing novel treatments for osteoporosis and other bone mass disorders characterized by loss of bone.

The low-density lipoprotein receptor related protein 5 (LRP5) had been previously identified as a target for the development of osteoporosis therapeutics based on its genomic proximity to the osteoporosis pseudoglioma syndrome (OPG) locus and the observation that LRP5 loss-of-function mutations are associated with OPG (Hey et al., Gene 216: 103-111 (1998); Gong et al., Cell 107: 513-523 (2001)). In addition, Kato et al. (J. Cell Biol. 157: 303-314 (2002)) demonstrated that null mutations of LRP5 in mice resulted in severe bone loss, further indicating that LRP5 had a role in the maintenance of sufficient bone mass. It has been shown that LRP5 and its homologue LRP6 are activators of the Wingless (Wnt) signaling pathway and that the various Dickkopf (Dkk) proteins inhibit the Wnt signaling pathway by binding to LRP5 or LRP6.

A role for LRP5 in glucose/lipid/fat metabolism was also disclosed in WO 98/46743 to Todd et al. which showed an LRP5 gene polymorphism in a patient with type I (insulin dependent) diabetes. This role is supported in Fujino et al., Proc. Natl. Acad. Sci. USA, 100: 229-34 (2003) which showed that LRP5 null mutation mice who are maintained on a high fat diet suffer from hypercholesterolemia and impaired glucose metabolism Hypercholesterolemia, impaired fat tolerance, and advanced atherosclerosis were also observed in LRP5 (−/−) mice who were also null for the Apo-lipoprotein E gene (Magoori et al., J. Biol. Chem. 278: 11331-36 (2003)). Interestingly, a recent report documented the negative regulatory role for Wnt signaling, a downstream mediator of LRP5 signaling, in adipogenesis (Bennett et al., J. Biol. Chem. 277: 30998-1004 (2002)). The above observations demonstrate a role for LRP5 and Wnt signaling in cholesterol, glucose, and fat metabolism in addition to their role in bone formation. Thus, the methods disclosed herein for identifying analytes which are modulators of Dkk-4 mediated signaling would also be useful for identifying analytes which could be used for treating disorders of cholesterol, glucose and fat metabolism, including, but not limited to, diabetes, hypercholesterolemia, and obesity.

Dkk-4 belongs to the Dickkopf (Dkk) family of secreted proteins which comprises Dkk-1, Dkk-2, Dkk-3, and Dkk-4. Dkk-1 has been shown to inhibit Wnt signaling by directly binding LRP5 and LRP6 (Semenov et al., Curr. Biol. 11: 951-961 (2001); Bafico et al., Nat. Cell Biol. 3: 683-686 (2001)). Dkk-2 has also been shown to inhibit Wnt signaling but only in the presence of kremen2. In the absence of kremen2, Dkk-2 activates Wnt signaling (Mao and Niehrs, Gene 302: 179-183 (2003). Dkk-3 can bind neither LRP6 or kremen (Mao and Niehrs, supra). Northern analysis of a panel of human tissues suggest that Dkk-4 is not expressed in embryonic or adult tissues; however, human cDNA libraries probed with a Dkk-4-specific probe suggest that Dkk-4 might be expressed in the cerebellum, activated human T-lymphocytes, lung, and esophagus (Krupnik et al., Gene 238: 301-313 (1999)). Although little is known about the function of Dkk-4, the close homology of Dkk-4 to Dkk-1 suggests it too might be an inhibitor of LRP5 and LRP6 signaling and thus, has a role in regulating the Wnt signaling pathway. This is supported by Mao and Niehrs, supra, which show that Dkk-4 appears to be similar to Dkk-1 with respect to Wnt inhibition and kremen cooperation.

In one aspect of the invention, the expression profile of Dkk-4 in human tissues and monkey bone was analyzed by TAQMAN PCR as described in Example 4. The results showed that Dkk-4 appears to be highly expressed in bone and is expressed to a lesser extent in cerebellum, whole brain, human testes, small intestine, and mammary gland (FIG. 7). This result was surprising in light of Krupnik et al., supra. In contrast to Dkk-4, the results showed that Dkk-1 appears to be preferentially expressed in placenta, cervix, and bladder (FIG. 5); however, Dkk-1 was also expressed in bone tissue. Like Dkk-4, Dkk-2 was expressed in bone tissue but unlike Dkk-4, Dkk-2 was expressed in a wide variety of other tissues as well (FIG. 6). LRP5 and LRP6 were expressed in a wide variety of tissues (FIGS. 8 and 9, respectively). The high expression of Dkk-4 in bone tissue shown in FIG. 7 and the observations that LRP5 loss-of-function mutations are associated with OPG, suggest that Dkk-4 is the desired molecular target for novel osteoanabolic treatments to replace bone lost via osteoporosis or other bone-loss disorders.

The isolated cDNA clones, associated vectors, hosts, recombinant subcellular fractions and membranes, and the expressed and mature forms of rhDkk-1 are useful for the identification of analytes that interfere with or alter the molecular and/or functional interaction between Dkk-1 and one or more of its receptors including LRP5 or 6, kremen1, and kremen2. The analytes can be used in therapeutic pharmaceutical compositions for the osteoanabolic treatment of disorders involving bone loss such as osteoporosis and fracture repair. Bone formation is stimulated by treating a patient who has suffered bone loss with an analyte (molecule, compound, composition, or drug), which inhibits binding of Dkk-4 to LRP5, LRP6, kremen1, kremen2, or combinations thereof. By inhibiting binding of Dkk-4 to LRP5, LRP6, kremen1, kremen2, or combinations thereof, the Wnt signaling pathway is activated which in turn stimulates or increases bone formation in the patient. To identify analytes that stimulate bone formation, the isolated cynomolgus monkey Dkk-4 (cDkk-4) protein is provided. The cDkk-4 is used in methods for identifying analytes which stimulate bone formation by antagonizing the association of Dkk-4 to one or more Dkk receptors including LRP5, LRP6, kremen1, and kremen2. Pharmaceutical compositions identified by the methods of the present invention may be used alone or in combination with inhibitors of bone resorption such as bisphosphonates, estrogens, selective estrogen receptor modulators (SERMs) and calcitonin.

Therefore, in light of the foregoing, the present invention provides nucleic acid molecules which encode the cynomolgus monkey Dickkopf 4 (cDkk-4) protein and provides methods for using the nucleic acid molecules and the cDkk-4 protein produced therefrom in assays for identifying analytes (molecules, compounds, drugs, or compositions) which modulate (interfere with, alter, enhance, repress, or suppress) the molecular or functional interaction between the cDkk-4 protein and one or more homologous or heterologous Dkk-4 receptors (for example, LRP5, LRP6, kremen1, and kremen2) and analytes in which the modulation stimulates bone formation (for example, activate the Wnt signaling pathway in bone tissue with the end result of stimulating bone formation).

Non-limiting examples of methods for identifying such analytes include (i) cell-based binding methods for identifying analytes which inhibit or suppress binding between cDkk-4 and one or more homologous or heterologous receptors such as LRP5, LRP5, kremen1, or kremen2 expressed in mammalian cells; (ii) cell-free binding methods for identifying analytes which inhibit or suppress binding between cDkk-4 and one or more homologous or heterologous receptors such as LRP5, LRP6, kremen1, kremen2, or extracellular domain thereof; (iii) osteoblast differentiation methods for identifying analytes which inhibit or suppress Dkk-4 inhibition of differentiation of preosteoblastic cells; and, (iv) cell-based reporter methods for identifying analytes which inhibit or suppress cDkk-4 inhibition of one or more homologous or heterologous receptors such as LRP5, LRP5, kremen1, or kremen2. Thus, the methods described herein are useful tools for identifying analytes which modulate molecular and/or functional interactions between cDkk-4 and one or more homologous or heterologous receptors. In particular, the methods described herein are useful for identifying analytes which are suppressors or inhibitors of Dkk-4 expression or interfere with, suppress, or inhibit Dkk-4/receptor interactions and thus, are activators of the Wnt signaling pathway involved in bone formation, for use in treatments for disorders characterized by bone loss. Such disorders include, but are not limited to, osteoporosis and other disorders characterized by bone loss. Although not wishing to be bound by theory, the identified modulators are useful for stimulating or increasing bone formation because the modulators antagonize the association between Dkk-4 and one or more Dkk receptors in a manner which activates the Wnt pathway. The analytes identified by the methods of the present invention are also useful for treatment of disorders of cholesterol or fat metabolism such as obesity and diabetes.

The present invention is particularly useful for identifying analytes of pharmaceutical importance which can be used in designing therapies or treatments for osteoporosis and other disorders which are characterized by bone loss wherein the object of the therapy or treatment is to both inhibit or suppress the bone loss and to stimulate formation of bone tissue to replace that bone which had been lost. Therefore, in one aspect of the present invention, an isolated nucleic acid molecule is provided which comprises a sequence of nucleotides encoding an RNA molecule which can be translated in vivo or in vitro to produce the cynomolgus monkey cDkk-4 protein with the amino acid sequence as set forth in SEQ ID NO:2 (FIG. 2). In further embodiments, the nucleic acid is substantially free from other nucleic acids of the cynomolgus monkey or substantially free from other nucleic acids. In a further embodiment, the isolated nucleic acid molecule comprises the nucleotide sequence set forth in SEQ ID NO:1 (FIG. 1).

The isolated nucleic acid molecules include both deoxyribonucleic acid (DNA) and ribonucleic acid (RNA) molecules encoding the cDkk-4 protein. The isolated nucleic acid molecules further include genomic DNA and complementary DNA (cDNA) encoding the cDkk-4 protein, either of which can be single- or double-stranded, as well as synthetic DNA, such as a synthesized, single stranded polynucleotide. When single-stranded, the DNA molecule can comprise either the coding (sense) strand or the non-coding (antisense) strand. For most cloning purposes, DNA is a preferred nucleic acid. In the case of nucleic acid molecules isolated from genomic DNA, the nucleic acid sequences encoding the Dkk-4 protein can be interrupted by one or more introns.

In further aspects of the present invention, cDkk-4 proteins are provided which have an amino acid sequence which is substantially similar to the amino acid sequence set forth SEQ ID NO:2 and nucleic acids which encode the cDkk-4 proteins for use in the analyte screening assays disclosed herein. Further provided are nucleic acids encoding the cDkk-4 protein which have a nucleotide sequence substantially similar to the nucleotide sequence set forth in SEQ ID NO:1. As used herein, the term "substantially similar" with respect to SEQ ID NO:2 means that the cDkk-4 protein contains mutations such as amino acid substitution or deletion mutations which do not abrogate the ability of the cDkk-4 protein to bind at least one of its receptors and suppress or inhibit Wnt signaling. The mutations include naturally occurring allelic variants and variants produced by recombinant DNA methods. As used herein, the term "substantially similar" with respect to SEQ ID NO:1 means that the cDkk-4 protein encoded by the nucleic acid contains mutations such as nucleotide substitution or deletion mutations which do not abrogate the ability of the cDkk-4 protein to bind at least one of its receptors and suppress or inhibit Wnt signaling. The mutations include naturally occurring allelic variants and variants produced by recombinant DNA methods. In general, any of the foregoing mutations which do not abrogate the ability of cDKK-4 protein to bind at least one of its homologous or heterologous Dkk-4 receptors are conservative mutations.

The present invention further includes biologically active fragments or mutants of SEQ ID NO:1. Any such biologically active fragment and/or mutant will encode either a polypeptide or polypeptide fragment which at least substantially mimics the properties or activity of the cDkk-4 protein, including but not limited to the cDkk-4 protein as set forth in SEQ ID NO:2. Any such polynucleotide includes, but is not limited to, nucleotide substitutions, deletions, additions, amino-terminal truncations, and carboxy-terminal truncations which do not substantially abrogate the properties or activities of the cDkk-4 protein produced therefrom. Thus, the mutations of the present invention encode mRNA molecules that express a cDkk-4 protein in a eukaryotic cell which has sufficient activity (ability to bind one or more of its receptors) to be useful in drug discovery.

The present invention further includes synthetic DNAs (sDNA) which encode the cDkk-4 protein wherein the nucleotide sequence of the sDNA differs from the nucleotide sequence of SEQ ID NO: 1 but still encodes the cDkk-4 protein as set forth in SEQ ID NO:2. For example, to express or enhance expression of the cDkk-4 protein in a particular cell type, it may be necessary to change the sequence comprising one or more of the codons encoding the cDkk-4 protein to sequences which enable expression of the cDkk-4 protein in the particular cell type. Such changes include modifications for codon usage peculiar to a particular host or removing cryptic cleavage or regulatory sites which would interfere with expression of the cDkk-4 protein in a particular cell type. Therefore, the present invention discloses codon redundancies which may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not alter or do not substantially alter the ultimate physical or functional properties of the expressed protein (in general, these mutations are referred to as conservative mutations). For example, substitution of valine for leucine, arginine for lysine, or asparagine for glutamine may not cause a change in the functionality of the polypeptide.

It is known that DNA sequences encoding a peptide may be altered so as to code for a peptide that has properties that are different than those of the naturally occurring peptide. Methods for altering the DNA sequences include, but are not limited to, site-directed mutagenesis. Examples of altered properties include, but are not limited to, changes in the affinity of an enzyme for a substrate or a receptor for a ligand.

Included in the present invention are DNA sequences that hybridize to SEQ ID NO: 1 under stringent conditions. By way of example, and not limitation, a procedure using conditions of high stringency is as follows. Prehybridization of filters containing DNA is carried out for about 2 hours to overnight at about 65° C. in buffer composed of 6×SSC, 5×Denhardt's solution, and 100 μg/ml denatured salmon sperm DNA. Filters are hybridized for about 12 to 48 hrs at 65° C. in prehybridization mixture containing 100 μg/ml denatured salmon sperm DNA and 5-20×106 cpm of 32P-labeled probe. Washing of filters is done at 37° C. for about 1 hour in a solution containing 2×SSC, 0.1% SDS. This is followed by a wash in 0.1×SSC, 0.1% SDS at 50° C. for 45 minutes before autoradiography. Other procedures using conditions of high stringency would include either a hybridization step carried out in 5×SSC, 5×Denhardt's solution, 50% formamide at about 42° C. for about 12 to 48 hours or a washing step carried out in 0.2×SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, 3$^{rd}$ Edition. Cold Spring Harbor Laboratory Press, Plainview, N.Y. (2001). In addition to the foregoing, other conditions of high stringency which may be used are also well known in the art.

In an another aspect of the present invention, a substantially purified form of a cDkk-4 protein which comprises a sequence of amino acids as disclosed in FIG. 2 (SEQ ID NO:2) is provided. Further provided are biologically active fragments and/or mutants of the cDkk-4 protein, which comprise at least a portion of the amino acid sequence set forth in SEQ ID NO: 2. These mutations or fragments include, but not limited to, amino acid substitutions, deletions, additions, amino terminal truncations, and carboxy-terminal truncations such that these mutations provide for proteins or protein fragments of diagnostic, therapeutic, or prophylactic use and are useful for screening assays for identifying analytes which interfere with the interaction of cDkk-4 and one or more homologous or heterologous receptors, such analytes being useful for treatment of osteoporosis or other conditions characterized by aberrant bone mass and/or bone loss and treatment of disorders of cholesterol or fat metabolism such as obesity and diabetes. In a particular embodiment, the present invention provides an isolated nucleic acid molecule comprising a sequence which encodes a mutated cDkk-4 protein comprising the sequence set forth in SEQ ID NO:2 with about 1-10 amino acid additions, deletions, or substitutions, wherein the mutated cDkk-4 polypeptide binds at least a homologous or heterologous LRP5, preferably a human LRP5.

The cDkk-4 proteins of the present invention can be the "mature" protein or a fragment or portion thereof, any of which can be a part of a larger protein such as a fusion protein. It is often advantageous to include covalently linked to the amino acid sequence of the cDkk-4 protein, an additional amino acid sequence which contains secretory or leader sequences, pro-sequences, sequences which aid in purification of the cDkk-4 proteins such as multiple histidine residues (polyHis) or antibody-binding epitopes, or one or more additional amino acid sequences which confer stability to the cDkk-4 protein during recombinant production. Thus, cDkk-4 fusion proteins are provided which comprise all or part of the cDkk-4 protein linked at its amino or carboxyl terminus to proteins or polypeptides such as green fluorescent protein (GFP), c-myc epitope, alkaline phosphatase, protein A or G, glutathione S-transferase (GST), polyHis, peptide cleavage site, or antibody Fc region. Any such fusion construct can be expressed in a cell line of interest and used to screen for modulators of the cDkk-4 protein disclosed herein. In a particular embodiment, the present invention provides an isolated nucleic acid molecule comprising a sequence which encodes a fusion cDkk-4 protein comprising the sequence set forth in SEQ ID NO:2 or a fusion proteins with about 1-10 amino acid additions, deletions, or substitutions, wherein the mutated cDkk-4 protein binds at least a homologous or heterologous LRP5, preferably a heterologous LRP5 such as a human LRP5.

The present invention further provides vectors which comprise at least one of the nucleic acid molecules disclosed throughout this specification, preferably wherein the nucleic acid molecule is operably linked to a heterologous promoter. These vectors can comprise DNA or RNA. For most cloning purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses the cDkk-4 protein, polypeptide fragment thereof, or fusion protein comprising all or part of the cDkk-4 protein encoded therein. It is well within the purview of the skilled artisan to determine an appropriate vector for a particular gene transfer or other use. As used herein, the term "recombinant Dkk-4 protein" is intended to include any variation of cDkk-4 protein disclosed herein which is expressed from a vector transfected into a eukaryote cell or transformed into a prokaryote cell. Transfected eukaryote cells and transformed prokaryote cells are referred to as recombinant host cells.

An expression vector containing DNA encoding a cDkk-4 protein or any one of the aforementioned variations thereof wherein the DNA is preferably operably linked to a heterologous promoter can be used for expression of the recombinant cDkk-4 protein in a recombinant host cell. Such recombinant host cells can be cultured under suitable conditions to produce recombinant cDkk-4 protein or a biologically equivalent form. Expression vectors include, but are not limited to, cloning vectors, modified cloning vectors, specifically designed plasmids, or specifically designed viruses.

Commercially available mammalian expression vectors which are suitable for recombinant cDkk-4 protein expression include, but are not limited to, pcDNA3.neo (Invitrogen, Carlsbad, Calif.), pcDNA3.1 (Invitrogen), pcDNA3.1/Myc-His (Invitrogen), pCI-neo (Promega, Madison, Wis.), pLITMUS28, pLITMUS29, pLITMUS38 and pLITMUS39 (New England Bioloabs, Beverly, Mass.), pcDNAI, pcDNAIamp (Invitrogen), pcDNA3 (Invitrogen), pMC1neo (Stratagene, La Jolla, Calif.), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

Also, a variety of bacterial expression vectors can be used to express recombinant cDkk-4 protein in bacterial cells. Commercially available bacterial expression vectors which may be suitable for recombinant cDkk-4 protein expression include, but are not limited to, pCR2.1 (Invitrogen), pET11a (Novagen, Madison, Wis.), lambda gt11 (Invitrogen), and pKK223-3 (Pharmacia).

In addition, a variety of fungal cell expression vectors may be used to express recombinant cDkk-4 protein in fungal cells. Commercially available fungal cell expression vectors which are suitable for recombinant cDkk-4 protein expression include, but are not limited to, pYES2 (Invitrogen) and *Pichia* expression vector (Invitrogen).

Also, a variety of insect cell expression vectors can be used to express recombinant cDkk-4 protein in insect cells. Commercially available insect cell expression vectors which can be suitable for recombinant expression of cDkk-4 protein include, but are not limited to, pBlueBacIII and pBlueBacHis2 (Invitrogen), and pAcG2T (Pharmingen).

Viral vectors which can be used for expression of recombinant cDkk-4 protein include, but are not limited to, adenovirus vectors, adeno-associated virus vectors, herpesvirus vectors, Sindbis virus vectors, Simliki forest virus vectors, pox virus vectors (such as vaccinia virus, fowl pox, canary pox, and the like), retrovirus vectors, and baculovirus vectors. Many of viral vectors are commercially available.

The present invention further provides recombinant host cells transformed or transfected with a vector comprising any one of the aforementioned nucleic acid molecules, particularly host cells transformed or transfected with a vector comprising any one of the aforementioned nucleic acid molecules wherein the nucleic acid molecule is operably linked to a promoter. Recombinant host cells include bacteria such as *E. coli,* fungal cells such as yeast, plant cells, mammalian cells including, but not limited to, cell lines of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Also, mammalian species which may be suitable and which are commercially available, include but are not limited to, L cells L-M(TK-) (ATCC CCL-1.3), L cells L-M (ATCC CCL-1.2), Saos-2 cells (ATCC HTB-85), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-KL cells (ATCC CCL-61), 3T3 cells (ATCC CCL-92), NIH/3T3 cells (ATCC CRL-1658), HeLa cells (ATCC CCL-2), C127I cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IFO50415), and CPAE cells (ATCC CCL-209). Such recombinant host cells can be cultured under suitable conditions to produce cDkk-4 protein or a biologically equivalent form.

As noted above, an expression vector containing DNA encoding cDkk-4 protein or any one of the aforementioned variations thereof can be used to express the cDkk-4 protein encoded therein in a recombinant host cell. Therefore, the present invention provides a process for expressing a cDkk-4 protein or any one of the aforementioned variations thereof in a recombinant host cell comprising introducing the vector comprising a nucleic acid which encodes the cDkk-4 protein into a suitable host cell and culturing the host cell under conditions which allow expression of the cDkk-4 protein. In a further embodiment, the cDkk-4 protein has an amino acid sequence substantially as set forth in SEQ ID NO:2 and binds at least one homologous or heterologous Dkk-4 receptor such as LRP5, and the nucleic acid encoding the cDkk-4 protein is operably linked to a heterologous promoter which can be constitutive or inducible. Thus, the present invention further provides a cell comprising a nucleic acid encoding the cDkk-4 protein which has an amino acid sequence substantially as set forth in SEQ ID NO:2, which preferably binds at least one homologous or heterologous receptor such as LRP5, and wherein the nucleic acid encoding the cDkk-4 protein is operably linked to a promoter.

The nucleic acids of the present invention are preferably assembled into an expression cassette that comprises sequences which provide for efficient expression of the cDkk-4 protein or variant thereof encoded thereon in a human cell. The cassette preferably contains the full-length cDNA encoding the cDkk-4 protein or a DNA encoding a fragment of the cDkk-4 protein with homologous or heterologous transcriptional and translational control sequences operably linked to the DNA. Such control sequences include at least a transcription promoter (constitutive or inducible) and transcription termination sequences and can further include other regulatory elements such as transcription enhancers, ribosome binding sequences, splice junction sequences, and the like. In most embodiments, the promoter is a heterologous promoter, however, in particular embodiments, the promoter can the natural cDkk-4 promoter for ectopic expression of the cDkk-4 in various host cells of non-cynomolgus monkey origin. In a particularly useful embodiment, the promoter is the constitutive cytomegalovirus immediate early promoter with or without the intron A sequence (CMV) although those skilled in the art will recognize that any of a number of other known promoters such as the strong immunoglobulin promoter, Rous sarcoma virus long terminal repeat promoter, SV40 small or large T antigen promoter, or the like. A preferred transcriptional terminator is the bovine growth hormone terminator although other known transcriptional terminators such as SV40 termination sequences can also be used. The combination of an expression cassette comprising the cDkk-4 gene operably linked to the CMV promoter and the BGH terminator has been found to provide suitable expression of cDNA encoding the cDkk-4 protein in eukaryote cells (See plasmid pcDNA3.1/Dkk-4/Myc-His-direct14 of Example 3).

Following expression of cDkk-4 protein or any one of the aforementioned variations of the cDkk-4 protein in a host cell, cDkk-4 protein or variant thereof can be recovered to provide cDkk-4 protein in a form capable of binding one or more homologous or heterologous Dkk receptors. Several cDkk-4 protein purification procedures are available and suitable for use. The cDkk-4 protein can be purified from cell lysates and extracts by various combinations of, or individual application of salt fractionation, ion exchange chromatography, size exclusion chromatography, hydroxylapatite adsorption chromatography, or hydrophobic interaction chromatography. In addition, cDkk-4 protein can be separated from other cellular polypeptides by use of an immunoaffinity column made with monoclonal or polyclonal antibodies specific for cDkk-4 protein or a particular epitope thereof. Alternatively, in the case of fusion polypeptides comprising all or a portion of the cDkk-4 protein fused to a second polypeptide, purification can be achieved by affinity chromatography comprising a reagent specific for the second polypeptide such as an antibody or metal.

Cloning, expression vectors, transfections and transformations, and protein isolation of expressed proteins are well known in the art and have been described, for example, in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, $3^{rd}$ Edition. Cold Spring Harbor Laboratory Press, Plainview, N.Y. (2001). For example, any of a variety of procedures may be used to clone DNA encoding cDkk-4 protein from RNA isolated from the cynomolgus monkey. These methods include, but are not limited to, the method shown in Examples 1-3 and the following methods.

(1) RACE PCR cloning methods such as disclosed in Frohman et al., Proc. Natl. Acad. Sci. USA 85: 8998-9002 (1988)). 5' and/or 3' RACE can be performed to generate a full-length cDNA sequence. This strategy involves using gene-specific oligonucleotide primers for PCR amplification of cDkk-4 cDNA. These gene-specific primers are designed through identification of an expressed sequence tag (EST) nucleotide sequence which has been identified by searching any number of publicly available nucleic acid and protein databases.

(2) Direct functional expression of the cDkk-4 cDNA following the construction of a cDkk-4-containing cDNA library in an appropriate expression vector system.

(3) Screening a cDkk-4-containing cDNA library constructed in a bacteriophage or plasmid shuttle vector with a labeled degenerate oligonucleotide probe designed from the amino acid sequence of the cDkk-4 protein.

(4) Screening a cDkk-4-containing cDNA library constructed in a bacteriophage or plasmid shuttle vector with a partial cDNA encoding the cDkk-4 polypeptide. This partial cDNA is obtained by the specific PCR amplification of cDkk-4 DNA fragments through the design of degenerate oligonucleotide primers from the amino acid sequence known for other membrane proteins which are related to the cDkk-4 polypeptide.

(5) Screening a cDkk-4-containing cDNA library constructed in a bacteriophage or plasmid shuttle vector with a partial cDNA or oligonucleotide with homology to a mammalian cDkk-4 protein. This strategy may also involve using gene-specific oligonucleotide primers for PCR amplification of cDkk-4 cDNA identified as an EST as described above.

(6) Designing 5' and 3' gene specific oligonucleotides using SEQ ID NO: 1 as a template so that either the full-length cDNA can be generated by known RACE techniques or a portion of the coding region can be generated by these same known RACE techniques to generate and isolate a portion of the coding region to use as a probe to screen one of numerous types of cDNA and/or genomic libraries in order to isolate a full-length version of the nucleotide sequence encoding cDkk-4.

It would be readily apparent to those skilled in the art that other types of libraries, as well as libraries constructed from other cell types or species types, may be useful for isolating a cDkk-4-encoding DNA or a cDkk-4 homologue. Other types of libraries include, but are not limited to, cDNA libraries derived from other cells. The selection of cells or cell lines for use in preparing a cDNA library to isolate a cDNA encoding cDkk-4 can be done by first measuring cell-associated cDkk-4 activity using any known assay available for such a purpose.

Preparation of cDNA libraries can be performed by standard techniques well known in the art. Well known cDNA library construction techniques can be found for example, in Sambrook et al., Molecular Cloning: A Laboratory Manual 2nd Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). Complementary DNA libraries may also be obtained from numerous commercial sources, including but not limited to Clontech Laboratories, Inc. (Palo Alto, Calif.) and Stratagene (La Jolla, Calif.).

The DNA molecules, RNA molecules, and recombinant polypeptides of the present invention can be used to screen and measure levels of cDkk-4 expression in homologous or heterologous cells. The recombinant polypeptides, DNA molecules, and RNA molecules lend themselves to the formulation of kits suitable for the detection and typing of cDkk-4 proteins. Such a kit would comprise a compartmentalized carrier suitable to hold in close confinement at least one container. The carrier would further comprise reagents such as recombinant cDkk-4 or anti-cDkk-4 antibodies suitable for detecting cDkk-4 proteins. The carrier may also contain a means for detection such as labeled antigen or enzyme substrates or the like. The kit enables identification of polymorphic forms of cDkk-4 protein which can then be used in the previously described methods to determine the effect the polymorphism has on binding between the polymorphic cDkk-4 protein and a homologous or heterologous Dkk receptor and on the Wnt signaling pathway.

In accordance with yet another embodiment of the present invention, there are provided antibodies having specific affinity for the cDkk-4 protein or epitope thereof. The term "antibodies" is intended to be a generic term which includes polyclonal antibodies, monoclonal antibodies, Fab fragments, single $V_H$ chain antibodies such as those derived from a library of camel or llama antibodies or camelized antibodies (Nuttall et al., Curr. Pharm. Biotechnol. 1: 253-263 (2000); Muyldermans, J. Biotechnol. 74: 277-302 (2001)), and recombinant antibodies. The term "recombinant antibodies" is intended to be a generic term which includes single polypeptide chains comprising the polypeptide sequence of a whole heavy chain antibody or only the amino terminal variable domain of the single heavy chain antibody ($V_H$ chain polypeptides) and single polypeptide chains comprising the variable light chain domain ($V_L$) linked to the variable heavy chain domain ($V_H$) to provide a single recombinant polypeptide comprising the Fv region of the antibody molecule (scFv polypeptides)(See, Schmiedl et al., J. Immunol. Meth. 242: 101-114 (2000); Schultz et al., Cancer Res. 60: 6663-6669 (2000); Dübel et al., J. Immunol. Meth. 178: 201-209 (1995); and in U.S. Pat. No. 6,207,804 B1 to Huston et al.). Construction of recombinant single $V_H$ chain or scFv polypeptides which are specific against an analyte can be obtained using currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. In further embodiments, the recombinant antibodies include modifications such as polypeptides having particular amino acid residues or ligands or labels such as horseradish peroxidase, alkaline phosphatase, fluors, and the like. Further still embodiments include fusion polypeptides which comprise the above polypeptides fused to a second polypeptide such as a polypeptide comprising protein A or G.

The antibodies specific for cDkk-4 protein can be produced by methods known in the art. For example, polyclonal and monoclonal antibodies can be produced by methods well known in the art, as described, for example, in Harlow and Lane, Antibodies: A Laboratory Manual. Cold Spring Harbor Laboratory Press: Cold Spring Harbor, N.Y. (1988). cDkk-4 proteins or fragments thereof can be used as immunogens for generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, camelized, CDR-grafted, or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (See, for example, Bahouth et al., Trends Pharmacol. Sci. 12: 338 (1991); Ausubel et al., Current Protocols in Molecular Biology (John Wiley and Sons, N.Y. (1989)).

Antibodies so produced can be used for the immunoaffinity or affinity chromatography purification of the cDkk-4 protein or cDkk-4 protein/receptor complexes. The above referenced anti-cDkk-4 protein antibodies can also be used to modulate the activity of the cDkk-4 protein in living animals, in humans, or in biological tissues isolated therefrom. Accordingly, contemplated herein are compositions comprising a carrier and an amount of an antibody having specificity for cDkk-4 protein effective to block naturally occurring cDkk-4 protein from binding to a Dkk receptor, which results in modulation of the Wnt signaling pathway such that bone growth is stimulated.

Therefore, the nucleic acids encoding cDkk-4 protein or variant thereof, vectors containing same, host cells transformed with the nucleic acids or vectors which express the cDkk-4 protein or variants thereof, the cDkk-4 protein and variants thereof, as well as antibodies specific for cDkk-4 protein, can be used in in vivo or in vitro methods for screening a plurality of analytes to identify analytes which are modulators of the cDkk-4 protein/receptor interaction. These methods provide information regarding the function and activity of the cDkk-4 protein and variants thereof which can lead to the identification and design of molecule, compounds, or compositions capable of specific interactions with human Dkk-4 protein. In preferred embodiments, the methods identify analytes which interfere with the binding of the cDkk-4 protein to a homologous or heterologous Dkk receptor involved in the Wnt signaling pathway. Thus, the methods identify analytes which inhibit or suppress Dkk-4 protein suppression of Wnt signaling. Such analytes are useful either alone or in combination with other compounds for treating osteoporosis and other disorders characterized by bone loss or treating disorders of cholesterol or fat metabolism such as obesity and diabetes.

Accordingly, the present invention provides methods (screening assays) for identifying analytes which modulate the binding of cDkk-4 protein to one or more homologous or heterologous Dkk receptors (for example, LRP5, LRP6, kremen1 or kremen2). That is, screening method for identifying candidate or test compounds or agents, for example, peptides, peptidomimetics, small molecules or other drugs. Modulators can include, for example, agonists and/or antagonists. In a particularly preferred embodiment, the present invention provides methods for identifying analytes which modulate binding of cDkk-4 protein to LRP5 and Kremen2.

The term "agonist" refers to an agent that mimics or upregulates (for example, potentiates or supplements) cDkk-4 protein bioactivity (and, therefore, human Dkk-4 activity). An agonist can be an analyte which mimics a bioactivity of cDkk-4 protein, such as transduction of a signal from a Dkk receptor, by, for example, interacting with a human Dkk receptor. An agonist can also be an analyte that upregulates expression of cDkk-4 protein. An agonist can also be an analyte which modulates the expression or activity of a protein which is located downstream, for example, of a Dkk receptor, thereby mimicking or enhancing the effect of binding of cDkk-4 protein to the Dkk receptor.

The term "antagonist" refers to an agent that inhibits, decreases, or suppresses a bioactivity of cDkk-4 protein (and, therefore, human Dkk-4 protein). An antagonist can be a compound which decreases signaling from cDkk-4 protein, for example, an analyte that is capable of binding to cDkk-4 protein or a Dkk receptor. A preferred antagonist inhibits or suppresses the interaction between cDkk-4 protein (and, therefore, human cDkk-4 protein) and another molecule, such as a Dkk receptor. Alternatively, an antagonist can be a compound that downregulates expression of the Dkk-4 gene. An antagonist can also be a compound which modulates the expression or activity of a protein which is located downstream of a Dkk receptor, thereby antagonizing the effect of binding of Dkk-4 protein to a Dkk receptor.

In preferred embodiments, the screening methods disclosed herein are useful for identifying analytes which bind to the site or domain of cDkk-4 protein that is involved in binding to a particular Dkk receptor or to a site or domain on the Dkk receptor which is involved in binding to the cDkk-4 protein. In either case, the screening methods identify analytes which interfere with the binding of cDkk-4 protein to a Dkk receptor. The interference in binding can be measured directly by identifying the cDkk-4 protein/Dkk receptor complex or indirectly by monitoring a downstream cellular response to the interference in binding such as activation of a reporter gene responsive to the interference in binding or a cellular marker that is expressed in cells induced to differentiate into osteoblasts.

As used herein, the Dkk receptor can be a receptor specific for cDkk-4 protein, Dkk protein, or both. The Dkk receptor further includes receptors which can bind one or more of Dkk-1 protein, Dkk-2 protein, Dkk-3 protein, or Dkk-4 protein.

In a preferred embodiment, the method identifies analytes which activate Wnt signaling by inhibiting or suppressing Dkk-4 protein binding to a homologous or heterologous Dkk receptor such as LRP5 or LRP6. In a further embodiment, the method identifies analytes which activate Wnt signaling by inhibiting or suppressing Dkk-4 protein binding to a homologous or heterologous Dkk receptor such as LRP5 or LRP6 in combination with homologous or heterologous kremen1 or kremen2. Methods for identifying analytes which modulate (interfere with, inhibit, suppress, or stimulate) binding of cDkk-4 protein to one or more homologous or heterologous Dkk receptors (preferably, a heterologous Dkk receptor, most preferably a heterologous Dkk receptor of human origin) include (i) cell-based binding methods for identifying analytes which inhibit binding between cDkk-4 protein and at least one homologous or heterologous Dkk receptor such as LRP5, LRP5, kremen1, or kremen2 expressed in mammalian cells; (ii) cell-free binding methods for identifying analytes which inhibit binding between cDkk-4 and at least one homologous or heterologous Dkk receptor such as LRP5, LRP6, kremen1, kremen2, or extracellular domain thereof; (iii) cell-based osteoblast differentiation methods for identifying analytes which inhibit or suppress Dkk-4 protein inhibition of differentiation of preosteoblastic cells; and, (iv) cell-based reporter methods for identifying analytes which modulate cDkk-4 protein inhibition of at least one Dkk receptor such as LRP5, LRP5, kremen1 or kremen2. The cDkk-4 protein and the human Dkk-4 protein differ by 10 amino acids (See FIG. 4). Therefore, while the methods disclosed herein use the cDkk-4 protein and nucleic acids encoding the same, the Dkk receptor (for example, LRP5, LRP6, kremen1, and kremen2) and nucleic acids encoding the same as well as other proteins and nucleic acids encoding proteins comprising the Wnt signaling pathway such as Wnt protein are not limited to those obtained from the cynomolgus monkey but can include those polypeptides and nucleic acids encoding the same from other mammals such as humans.

In one embodiment, the invention provides methods for screening a plurality of analytes for analytes which bind to or modulate the activity of cDkk-4 protein or polypeptide or biologically active portion thereof. In another embodiment, the invention provides methods for screening a plurality of analytes for analytes which bind to or modulate the activity of a Dkk receptor. The plurality of analytes can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, Anticancer Drug Des. 12: 145 (1997)). Examples of methods for synthesizing molecular libraries can be found in the art, for example, DeWitt et al., Proc. Natl. Acad. Sci. USA 90: 6909 (1993); Erb et al., Proc. Natl. Acad. Sci. USA 91: 11422 (1994); Zuckermann et al., J Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994).

Libraries of analytes can be presented in solution (for example, Houghten, Biotech. 13: 412-421 (1992)), or on beads (Lam, Nature 354: 82-84 (1991)), chips (Fodor Nature, 364: 555-556 (1993)), bacteria or spore (U.S. Pat. No. 5,223,409 to Ladner), plasmids (Cull et al., Proc Natl. Acad. Sci. USA 89: 1865-1869 (1992)) or on phage (Scott and Smith, Science 249: 386-390 (1990); Devlin, Science 249: 404406 (1990); Cwirla et al., Proc. Natl. Acad. Sci. USA 87: 6378-6382 (1990); Felici J. Mol. Biol. 222:301-310(1991); and, U.S. Pat. No. 5,223,409 to Ladner).

In the various embodiments of the cell-based and cell-free methods disclosed herein, the Dkk receptor is preferably obtained from an organism selected from the group consisting of *Xenopus,* mouse, rat, and human. More preferably, the Dkk receptor is of human origin. The Dkk receptor is preferably selected from the group consisting of LRP5, LRP6, kremen1, and kremen2. For many of the methods disclosed herein, the preferred Dkk receptor is LRP5 or LRP6; however, some aspects can further include Icremen1 or kremen2. Therefore, in a particularly preferred aspect, the method includes Dkk receptors LRP5 or LRP6 and Kremen 1 and/or 2. In a particularly preferred aspect, the method includes LRP5 or 6 and Kremen2. Many cell-based methods can further include other components of the Wnt pathway such as Wnt protein, Dishevelled protein, and Frizzled protein. Vectors that express the human LRP5 receptor have been disclosed in U.S. Pat. No. 6,555,654 to Todd et al.; WO02/092015 to Allen et al.; Mao et al., Cell 107: 513-523 (2001); and, Mao et al., Mol. Cell 7: 801-809 (2001) and vectors that express the human LRP6 receptor are disclosed in Mao et al., Nature 411: 321-325 (2001). Particular methods further include expression vectors which express the Wnt protein. Wnt protein expression vectors have been disclosed in Mao et al., Cell 107: 513-523 (2001); Mao et al., Nature 411: 321-325 (2001); and Boyden et al., N. Eng. J. Med. 346: 1513-1521 (2002). Expression vectors which express kremen1 and kremen2 have been disclosed in Mao and Niehers, Gene 302: 179-183 (2003) and Mao et al., Nature 417: 664-667 (2002).

In one embodiment of a cell-based method, a recombinant cell which expresses a homologous or heterologous Dick receptor on the cell surface is contacted with cDkk-4 protein, to form a mixture. The mixture is then contacted with an analyte and the ability of the analyte to interact with a Dkk receptor is determined. The ability of the analyte to interact with a Dkk receptor comprises determining the ability of the analyte to preferentially bind to the Dkk receptor as compared to the ability of cDkk-4 protein to bind to the receptor. In another embodiment, a recombinant cell expressing a homologous or heterologous Dkk receptor on the cell surface is contacted with a mixture comprising an analyte and cDkk-4 protein and the ability of the analyte to interact with the Dkk receptor is determined. In a further still embodiment, a recombinant cell expressing a homologous or heterologous Dkk receptor on the cell surface is contacted with the analyte to form a mixture. The mixture is then contacted with the cDkk-4 protein and the ability of the analyte to inhibit the cDkk-4 protein from binding the Dkk receptor is determined.

Determining ability of the cDkk-4 protein or the analyte to bind to the homologous or heterologous Dkk receptor on the cell surface can be accomplished by detecting the bound cDkk-4 protein or analyte. For example, labeled antibodies specific for the cDkk-4 protein or the analyte can be used to detect binding or the Dkk-4 protein or analyte can be labeled directly with a label. In further embodiments, the cDkk-4 protein can be a fusion protein in which the amino or carboxyl terminus of the cDkk-4 is covalently linked to a detectable polypeptide, including but not limited to, myc or an enzyme such as a alkaline phosphatase, which can be detected in a colorimetric assay, or a detectable protein such as Green fluorescent protein. Determining the ability of the cDkk-4 protein to bind to a Dkk receptor in the presence of an analyte can also be accomplished by determining the activity of the receptor or an enzyme in a pathway responsive to the receptor. For example, the activity of the Dkk receptor can be determined by detecting induction of a cellular second messenger of the Dkk receptor (for example, intracellular $Ca^{2+}$, diacylglycerol, $IP_3$, alkaline phosphatase, and the like), detecting catalytic/enzymatic activity of the Dkk receptor on an appropriate substrate, detecting the induction of a reporter gene (comprising a Dkk-4 protein responsive regulatory element such as Wnt pathway inducible promoter such as the TCF binding sites operably linked to a nucleic acid encoding a detectable marker, for example, luciferase), or detecting a cellular response, for example, development, differentiation, or rate of proliferation.

Thus, in a particular embodiment, a cell-based binding method is provided which measures the ability of an analyte to modulate binding of cDkk-4 protein to a homologous or heterologous Dkk receptor on the surface of a mammalian cell transfected with one or more expression vectors which expresses the Dkk receptor (for example, one or more expression vectors selected from the group consisting of vectors which express LRP5, LRP6, kremen1, and kremen2). The transfected cells are incubated in medium containing cDkk-4 protein, preferably labeled with a reporter molecule such as alkaline phosphatase, radioactive isotope, lanthanide such as europium, or a fluorescent dye, and an analyte. After incubation, the medium is removed and the cells treated with a reagent which detects the cDkk-4 protein, for example a substrate and chromagen for detecting alkaline phosphatase activity, a labeled antibody specific for the cDkk-4 protein, or appropriate light wavelength to induce the fluorescent dye or lanthanide to emit light. A lack of detectable signal from the reagent indicates that the analyte interferes with the ability of the cDkk-4 protein to bind the cDkk receptor. Conversely, presence of detectable signal from the reagent indicates that the analyte has no apparent interfering effect on the ability of cDkk-4 protein to bind the Dkk receptor. Cell binding methods which can be modified to use the cDkk-4 protein are described in Mao et al., Nature 411: 321-325 (2001), Mao et al., Nature 417: 664-667 (2002).

By way of example, a suitable cell such the human HEK293T cell is transfected with one or more expression vectors, each of which expresses a Dkk receptor (for example, one or more expression vectors selected from the group consisting of vectors which express LRP5, LRP6, kremen1, and kremen2). Transfection can be performed using any one of transfection methods well known in the art, such methods including electroporation, LIPOFECTIN (Invitrogen), Calcium phosphate precipitation, DEAE-dextran, or FuGENE 6 (Roche Applied Sciences) and the transfected cells incubated for a time sufficient for expression of the Dkk receptor on the cell surface. In general, the transfected cells are incubated for about 48 hours at 37° C. and then incubated for about an hour at 37° C. in media containing cDkk-4 protein fused at the carboxy terminus with a protein such as alkaline phosphatase for enzymatic detection or myc for immunological detection with labeled antibodies specific for the myc and the analyte being tested for its ability to inhibit or suppress binding of the cDkk-4 to the receptor. In an alternative embodiment, the cDkk-4 is labeled with a radioactive or fluorescent molecule or is unlabeled and detection of bound cDkk-4 protein is via labeled antibodies against the cDkk-4 protein. After incubating the cells containing cDkk-4 protein, the cells are washed with a solution such as phosphate buffered saline and the cells reacted with a detection reagent suitable detecting the label. For example, the cells can be stained with Fast Red for detection of alkaline phosphatase label. The extent of inhibition or suppression of cDkk-4 protein binding to the Dkk receptor on the cell surface is inversely proportional to the amount of detection reagent on the cell surface. Variations of the cell binding method which have the object of detecting inhibitors or suppressors of cDkk-4 protein binding to a Dkk receptor on the cell surface are well within the purview of one of ordinary skill in the art.

In further embodiment of a cell-based method, modulators of Dkk-4 protein expression are identified by transfecting a cell with DNA encoding cDkk-4 protein operably linked to its naturally occurring promoter or a heterologous promoter which directs expression of a cDkk-4 protein (for example, the promoter which directs expression of the human Dkk-4 protein), contacting the transfected cell with an analyte, and measuring the expression of cDkk-4 mRNA or protein in the cell. The level of expression of cDkk-4 mRNA or protein in the presence of the analyte is compared to the level of expression of cDkk-4 mRNA or protein in the absence of the analyte. The analyte can then be identified as a modulator of Dkk-4 protein expression based on this comparison. For example, when expression of cDkk-4 mRNA or protein is greater (statistically significantly greater) in the presence of the analyte than in its absence, the analyte is identified as a stimulator of Dkk-4 mRNA or protein expression. Alternatively, when expression of cDkk mRNA or protein is less (statistically significantly less) in the presence of the analyte than in its absence, the analyte is identified as an inhibitor of Dkk-4 mRNA or protein expression. The level of cDkk-4 mRNA or protein expression in the cells can be determined by methods well known for detecting mRNA or proteins such as the methods described herein for detecting cDkk-4 mRNA or protein. Expression of mRNA can be determined by RT-PCR, preferably a real-time RT-PCR method such as that provided by TAQMAN RT-PCR, or Northern blotting. Protein expression can be determined by Western blotting.

A further embodiment of a cell-based method for screening for analytes which interfere with binding of cDkk-4 protein to a homologous or heterologous Dkk receptor is the two-hybrid system. The two-hybrid system is extremely useful for studying protein: protein interactions (See, Chien et al., Proc. Natl. Acad. Sci. USA 88: 9578-82 (1991); Fields et al., Trends Genetics 10: 286-92 (1994); Harper et al., Cell 75: 805-16 (1993); Vojtek et al., Cell 74: 205-14 (1993); Luban et al., Cell 73: 1067-78 (1993); Li et al., FASEB J. 7: 957-63 (1993); Zang et al., Nature 364: 308-13 (1993); Golemis et al., Mol. Cell. Biol. 12: 3006-14 (1992); Sato et al., Proc. Natl. Acad. Sci. USA 91: 9238-42 (1994); Coghlan et al., Science 267: 108-111 (1995); Kalpana et al., Science 266: 2002-6 (1994); Helps et al., FEBS Lett. 340: 93-8 (1994); Yeung et al., Genes & Devel. 8: 20879 (1994); Durfee et al., Genes & Devel. 7: 555-569 (1993); Paetkau et al., Genes & Devel. 8: 2035-45; Spaargaren et al., 1994 Proc. Natl. Acad. Sci. USA 91: 12609-13 (1994); Ye et al., Proc. Natl. Acad. Sci. USA 91: 12629-33 (1994); and U. S. Pat. Nos. 5,989,808; 6,251,602; and 6,284, 519) and can be adapted to screen for analytes which interfere with binding of cDkk-4 to one or more of its receptors.

The two-hybrid method relies upon the finding that the DNA binding and polymerase activation domains of many transcription factors, such as GAL4, can be separated and then rejoined to restore functionality (Morin et al., Nuc. Acids Res. 21: 2157-63 (1993)). While two-hybrid method is described with reference to the yeast system, it is understood that a two-hybrid screen can be conducted in other systems, for example systems which use prokaryote cells or mammalian cell lines.

An example of the two-hybrid method in yeast cells is as follows. Yeast strains with integrated copies of various reporter gene cassettes, such as for example GAL.fwdarw.LacZ, GAL.fwdarw.HIS3, or GAL.fwdarw.URA3 (Bartel, in Cellular Interactions and Development: A Practical Approach, 153-179 (1993); Harper et al., Cell 75: 805-16 (1993); Fields et al., Trends Genetics 10: 286-92 (1994)) are cotransformed with two plasmids, each expressing a different fusion protein. One plasmid encodes a fusion between cDkk-4 protein and the DNA binding domain (DBD) of, for example, the DBD of the GAL4 yeast transcription activator (Brent et al., Cell 43: 729-36 (1985); Ma et al., Cell 48: 847-53 (1987); Keegan et al., Science 231: 699-704 (1986)), while the other plasmid encodes a fusion between a cDkk receptor such as LRP5 or cytoplasmic fragment thereof and the RNA polymerase activation domain (AD) of the same transcription factor, for example, the AD of the GAL4 (Keegan et al., supra). The plasmids are transformed into a strain of the yeast that contains a reporter gene cassette such as the lacZ, whose regulatory region contains GAL4 binding sites. If the cDkk-4-DBD fusion protein is able to bind the Dkk receptor-AD fusion protein in the presence of a test analyte, they reconstitute a functional GAL4 transcription activator protein by bringing the two GAL4 components into sufficient proximity to activate transcription of the reporter gene. Thus, activation of transcription indicates that the analyte had no detectable effect on binding of cDkk-4 protein to a Dkk receptor. However, if an analyte interferes with the ability of the cDkk-4-DBD fusion protein to bind the Dkk receptor-AD fusion protein, the two GAL4 components are not brought into sufficient proximity to activate transcription of the reporter. Thus, no activation of transcription indicates that the analyte has an effect on cDkk-4 protein binding to a Dkk receptor.

Either hybrid protein alone is unable to activate transcription of the reporter gene, the DNA-binding domain hybrid, because it does not provide an activation function, and the activation domain hybrid, because it cannot localize to the GAL4 binding sites. The reporter gene cassettes consist of minimal promoters that contain the GAL4 DNA recognition site (Johnson et al., Mol. Cell. Biol. 4: 1440-8 (1984); Lorch et al., J. Mol. Biol. 186: 821-824 (1984)) cloned 5' to their TATA box. Transcription activation of the reporter is scored by measuring either the expression of β-galactosidase or the growth of the transformants on minimal medium lacking the specific nutrient that permits auxotrophic selection for the transcription product, for example, URA3 (uracil selection) or HIS3 (histidine selection) (See, Bartel, Cellular Interactions and Development: A Practical Approach, 153-179 (1993); Durfee et al., Genes & Devel. 7: 555-569 (1993); Fields et al., Trends Genet. 10: 286-292 (1994); and U.S. Pat. No. 5,283,173).

Additional methods of preparing two-hybrid assay systems which are suitable for identifying analytes which interfere with binding of cDkk-4 protein to a Dkk receptor would be evident to one of ordinary skill in the art (gee for example, Finley et al. in The Yeast Two-Hybrid System (Bartel et al., eds., Oxford, 1997); Meijia Yang in The Yeast Two-Hybrid System (Bartel et al., eds., Oxford, 1997); Gietz et al., Mol. & Cell. Biochem. 172: 67-9 (1997); Young, Biol. Reprod. 58: 302-311 (1998); Brent et al., Annu. Rev. Genet. 31: 663-704 (1997)).

Another cell-based method for screening analytes to identify analytes which interfere with binding of cDkk-4 protein to a homologous or heterologous Dkk receptor is a cell-based reporter assay. The cell-based reporter assay is a functional assay in which analytes are screened for the ability to activate a Wnt signaling pathway inhibited by cDkk-4 protein. A reporter gene under the control of a promoter specifically activated by Wnt signaling (a promoter containing one or more Wnt signaling-responsive transcription control factor elements or binding sites). An example of a promoter containing Wnt signaling-responsive transcription binding sites is the leukocyte enhancer factor-1 (LEF-1) responsive promoter (See Hsu et al., Molec. Cell. Biol. 18: 4807-4818 (1998)). The LEF-1 responsive promoter is one of many promoters responsive to various transcription factors of the lymphoid enhancer factor-T cell factor (EF/TCF) family. Reporter genes operably linked to the LEF-1 responsive promoter for studying protein interaction in the Wnt signaling pathway have been disclosed in Boyden et al., N. Eng. J. Med. 346: 1513-1521 (2002); Mao et al., Mol. Cell 7: 801-809 (2001); Hsu et al., Mol. Cell. Biol. 18: 4807-4818 (1998). Reporter genes which are useful in the cell-based assays of the present invention include, but are not limited to, the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites, particularly a promoter containing one or more elements responsive to one or more of the transcription factors of the LEF/TCF family.

A cell-based reporter assay which is exemplary comprises transfecting a suitable cell type such as one of those disclosed previously with expression vectors which separately express Wnt protein, LRP5 or LRP6, cDkk-4 protein, LEF-1 transcription factor (LEF-1 protein), and reporter gene operably linked to a LEF-1 responsive promoter. Preferably each expression vector constitutively expresses its protein. For example, each nucleic acid is operably linked to the CMV promoter. The cells are incubated in medium containing an analyte. Inhibition or suppression of cDkk-4 binding to LRP5 or LRP6 by the analyte is determined by activation of the Wnt signaling pathway which is measured by detecting expression of the reporter gene via the LEF-1 responsive reporter. In the absence of an analyte which inhibits or suppresses binding of cDkk-4 to LRP5 or LRP6, the cDkk-4 binds the LRP5 or LRP6. This prevents the LRP5 or LRP6 from binding the Wnt protein. The end result is that β-catenin does not form a complex with the LEF-1 protein and there is no activation of expression of the reporter gene via the LEF-1 responsive promoter. However, in the presence of an analyte which inhibits or suppresses binding of the cDkk-4 to LRP5 or LRP6, the LRP5 or LRP6 binds the Wnt protein. The end result is that β-catenin forms a complex with the LEF-1 protein; the complex then activates expression of the reporter via binding to the LEF-1 responsive promoter. Controls comprise the above transfected cells incubated in medium not containing the analyte and vectors for normalizing transfection. Further embodiments of the cell-based reporter assay include providing expression vectors which express kremen1 or kremen2. Thus, the assay includes measuring reporter gene expression in cells transfected with the reporter gene expression vector and any combination of expression vectors selected from the group consisting of vectors which express LRP5, LRP6, Wnt, cDkk-4, Dkk-1, kremen1, kremen2, and combinations thereof. For example, a combination of one or more vectors expressing cDkk-4, LRP5, LRP6, Kremen1, and Kremen2. In particular, a combination of vectors including cDkk-4, LRP5, LRP6, and Kremen2

A further still embodiment of a cell-based method for screening analytes to identify analytes which interfere with binding of cDkk-4 to a homologous or heterologous Dkk receptor is an osteoblast differentiation assay in which analytes are screened to identify analytes which inhibit or suppress the inhibitory effect of cDkk-4 on osteoblast differentiation. Katagiri et al., J. Cell Biol. 127: 1755-1766 (1994) and Yamaguchi et al., Biochem. Biophys. Res. Commun. 220: 366-371 (1996) have shown that adding exogenous growth factors to pluripotent marrow stromal cells induces the cells along an osteoblastic lineage. Gong et al. (Cell 107: 513-523 (2001) show that adding 300 ng/ml of BMP2 to the pluripotent mesenchymal cells C3H10T1/2 and ST2 results in expression of the osteoblastic markers alkaline phosphatase (ALP), Bglap, and Runx2. Gong et al. further show that ALP activity can be induced in C3H10T1/2 and ST2 cells by transfecting the cells with vectors expressing LRP5 and Wnt and that ALP activity can be induced in ST2 cells that are stably expressing LRP5 by transfecting the cells with a vector expressing Wnt. Thus, the Wnt signaling pathway is involved in differentiation of pluripotent cells along an osteoblast lineage. Therefore, because Dkk-1 and Dkk-4 can inhibit the Wnt signaling pathway by binding LRP5, the osteoblast differentiation assay of Gong et al. can be adapted to an assay which uses cDkk-4 to identify analytes which inhibit or suppress Dkk-4 inhibition of osteoblast differentiation.

An osteoblast differentiation assay which is exemplary comprises transfecting pluripotent cells such as C3H10T1/2 or ST2 cells with expression vectors which separately express cDkk-4, LRP5 or LRP6, and Wnt protein (for example, Wnt-1 or Wnt3 protein). The cells are incubated in medium containing the analyte and induction of ALP in the presence of the analyte is determined. Detection of ALP activity indicates that the analyte inhibits or suppresses binding of cDkk-4 to the Dkk receptor. Controls comprise the above cells incubated in medium without the analyte. Further embodiments include providing expression vectors which express kremen1 and kremen2 and transfecting the above cells with Kremen1 or kremen2. Thus, the osteoblast differentiation assay includes measuring ALP activity in cells transfected with any combination of expression vectors selected from the group consisting of vectors which express LRP5, LRP6, Wnt, cDkk-4, Dkk-1, kremen1, kremen2, and combinations thereof. In a particular embodiment, the method comprising transfecting the cells with vectors which express cDkk-4, Wnt protein, LRP5 and/or 6 and kremen2.

In one embodiment of a cell-free screening method, the method is a competition assay in which the ability of an analyte to effectively compete with the cDkk-4 protein for binding to a homologous or heterologous Dkk receptor is determined. Binding of the analyte can be determined either directly or indirectly. Binding can be determined using labeled or unlabeled antibodies against cDkk-4 protein, analyte, or Dkk receptor, the cDkk-4 protein-Dkk receptor complex, labeled cDkk-4 protein or Dkk receptor, and combinations thereof. Labels include, but are not limited to, radioactive isotopes, fluorescent dyes, enzymatic reporters such as alkaline phosphatase or horseradish peroxidase, donor-quencher fluorescent dyes, antibody recognition sites such as those provided by fusion polypeptides (for example, cDkk-4 protein fused to alkaline phosphatase or a myc antibody recognition sequence).

In a further embodiment, the method includes contacting the Dkk-4 protein with a Dkk receptor which binds cDkk-4 protein to form a mixture, adding an analyte to the mixture, and determining the ability of the analyte to interfere with the binding of the cDkk-4 to the Dkk receptor. Further embodiments include providing any combination of Dkk receptor selected from the group consisting of LRP5, LRP6, kremen1, kremen2, and combinations thereof, preferably, LRP5 or LRP6. In a further embodiment, the a combination of LRP5 and LRP6 together with Kremen1 and Kremen2 is provided. Immunoprecipitation is a particular type of cell-free method which is useful for identifying analytes which inhibit binding of cDkk-4 protein to one or more Dkk receptors.

In another embodiment of a cell-free method, the cDkk-4 protein is contacted with an analyte and the ability of the analyte to inhibit or suppress subsequent binding of the cDkk-4 protein to a homologous or heterologous Dkk receptor is determined. Determining the ability of the analyte to inhibit or suppress binding of the cDkk-4 protein can be detected as discussed above for cell-based methods. Determining the ability of the cDkk-4 protein to bind to a Dkk receptor can also be accomplished using a technology such as real-time Biomolecular Interaction Analysis (BIA) (Sjolander and Urbaniczky, Anal. Chem. 63:2338-2345 (1991) and Szabo et al., Curr. Opin. Struct Biol. 5: 699-705 (1995)). As used herein, "BIA" is a technology for studying biospecific interactions in real time, without labeling any of the interactants (for example, BIACORE). Changes in the optical phenomenon surface plasmon resonance (SPR) can be used as an indication of real-time reactions between biological molecules.

In many drug screening programs which screen libraries of analytes (drug, compounds, natural extracts, compositions, and the like), high throughput assays are desirable in order to maximize the number of analytes surveyed in a given period of time. Assays which are performed in cell-free systems, such as can be derived with purified or semi-purified proteins, are often preferred as "primary" screens in that they can be generated to permit rapid development and relatively easy detection of an alteration in a molecular target which is mediated by an analyte. Moreover, the effects of cellular toxicity and/or bioavailability of the analyte can be generally ignored in the in vitro system, the assay instead being focused primarily on the effect of the analyte on the molecular target as may be manifest in an alteration of binding affinity with upstream or downstream elements. Accordingly, in an exemplary screening method of the present invention, an analyte is contacted with cDkk-4 protein or a Dkk receptor. The Dkk-4 protein or Dkk receptor can be soluble, on a membrane surface, or immobilized on a solid substrate such as the surface of the wells of microtiter plate, bioassay chip, or the like. To the mixture of the analyte and the cDkk-4 protein or Dkk receptor is then added a composition containing a Dkk receptor or cDkk-4 protein, respectively. Detection and quantification of complexes of cDkk-4 protein and Dkk receptors in the presence of the analyte provide a means for determining an analyte's efficacy at inhibiting (or potentiating) complex formation between cDkk-4 protein and a Dick receptor. The efficacy of the analyte can be assessed by generating dose response curves from data obtained using various concentrations of the test compound. Moreover, a control can also be performed to provide a baseline for comparison. For the control, isolated and purified cDkk-4 protein or Dkk receptor is added to a composition containing the Dkk receptor or cDkk-4 protein and the formation of a cDkk-4/Dkk receptor complex is quantified in the absence of the analyte.

The cell-free methods herein are amenable to use of both soluble and/or membrane-bound forms of isolated proteins (for example, cDkk-4 protein or biologically active portions thereof or Dkk receptors). In the case of cell-free methods in which a membrane-bound form an isolated protein is used (for example, a Dkk receptor) it can be desirable to use a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON X-100, TRITON X-114, THESIT, Isotridecypoly(ethylene glycol ether)$_n$, 3-[(3-holamidopropyl)dimethylamino]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In particular embodiments of the above cell-free methods, it can be desirable to immobilize either cDkk-4 protein or a Dkk receptor to facilitate separation of cDkk-4 protein-Dkk receptor complexes from free cDkk-4 protein and Dkk receptor, as well as to accommodate automation of the method. Binding of analyte to cDkk-4 protein, or interaction of a cDkk-4 protein with a homologous or heterologous Dkk receptor in the presence and absence of an analyte, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/cDkk-4 fusion proteins or glutathione-S-transferase/Dkk receptor can be adsorbed onto glutathione SEPHAROSE beads (Sigma Chemical, St. Louis, Mo.) or glutathione-derivatized microtitre plates, which are then combined with the analyte or the analyte and either the non-adsorbed Dkk receptor or cDkk-4 protein, and the mixture incubated under conditions conducive to complex formation (for example, at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix and the level of cDkk-4 protein binding or activity determined using standard techniques.

Other methods for immobilizing proteins on matrices can also be used in the cell-free screening methods. For example, either cDkk-4 protein or a cDkk receptor can be immobilized using a conjugation of biotin and streptavidin. Biotinylated protein or target molecules can be prepared from biotin-NHS (N-hydroxy-succinimide) using techniques well known in the art (for example, the biotinylation kit available from Pierce Biotechnology, Rockford, Ill.), and immobilized in the wells of streptavidin-coated 96 well plates (Pierce Biotechnology). Alternatively, antibodies reactive with Dkk-4 protein or Dkk receptor but which do not interfere with binding of the cDkk-4 protein to a Dkk receptor can be derivatized to the wells of the plate, and unbound Dkk receptor or cDkk-4 protein trapped in the wells by antibody conjugation. Methods for detecting such complexes, in addition to those described above for the GST-immobilized complexes, include immunodetection of complexes using antibodies reactive with the cDkk-4 protein or Dkk receptor, as well as enzyme-linked assays which rely on detecting an enzymatic activity associated with the cDkk-4 protein or Dkk receptor.

A further embodiment of a cell-free binding method for identifying analytes which inhibit binding of cDkk-4 protein to one or more Dkk receptors such as those Dkk receptors selected from the group consisting of LRP5, LRP6, kremen1, kremen2, and combinations thereof, preferably, LRP5 or LRP6, or LRP5 or LRP6 and kremen2 is a modification of the GST fusion pull-down assay. The GST fusion pull-down assay has been described in Sambrook and Russell, Molecular Cloning: A Laboratory Manual 3rd Edition. Cold Spring Harbor Laboratory Press: Plainview, N.Y. (2001). A GST pull-down kit is available from Pierce Biotechnology. In the modified GST fusion pull-down assay used herein, either the DNA encoding cDkk-4 protein or Dkk receptor is cloned in-frame with the GST of a pGEX vector (Amersham Pharmacia Bioscience, Piscataway, N.J.) and expressed as a GST fusion protein in the BL21 *E. coli.* The expressed GST fusion protein is bound to immobilized reduced glutathione support. Preferably, the immobilized glutathione support is provided as a column. Labeled Dkk receptor or cDkk-4 protein (labeled protein), respectively, is incubated with the bound GST fusion protein in the presence of an analyte. Afterwards, unbound labeled protein is removed and the GST fusion protein bound or unbound to the labeled protein is eluted from the support with imidazole. The amount of labeled protein bound to the eluted GST fusion protein is determined by detecting the label. If the analyte interferes with cDkk-4 binding to the Dkk receptor, there will little or no detectable labeled protein eluted with the GST fusion protein compared to controls without the analyte. Conversely, if the analyte does not interfere with cDkk-4 binding to the Dkk receptor, the amount of labeled protein eluted with the GST fusion protein will be similar to the amount eluted in controls without the analyte.

It would be readily apparent to one of ordinary skill in the art that other cell-based or cell-free methods not disclosed herein can be adapted to used cDkk-4 to identify analytes which inhibit or suppress binding of cDkk-4 to one or more homologous or heterologous Dkk receptors. Therefore, the present invention is not limited to the methods disclosed herein but can include other assays provided the assay is adapted to use the cDkk-4 protein or nucleic acids disclosed herein.

The following examples are intended to promote a further understanding of the present invention without limiting the scope of the invention.

EXAMPLE 1

This example describes a method which was used to isolate RNA from cynomolgus monkey bone for preparing a cDNA library to screen for clones which encode the cDkk-4 protein.

Molecular procedures were performed following standard procedures well known in the art (See, e.g., Ausubel et. al., Short Protocols in Molecular Biology, F. M.,—2nd. ed., John Wiley & Sons, (1992) and Sambrook et al., Molecular Cloning: A Laboratory Manual 2nd Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). RNA was isolated from tibia using the PURESCRIPT RNA Isolation Kit (Gentra Systems, Inc., Minneapolis, Minn.).

For initial tissue preparation, the metaphysic and epifysis was dissected from tibia. The tibia was isolated and the metaphysis and epifysis parts were quickly removed. The metaphysis and epifysis parts of the bone was then separated from the surrounding muscle. The bone marrow was then washed out with 0.9% sodium chloride solution with a syringe and needle. Tibia metaphysis and epifysis parts were frozen in liquid nitrogen and stored at −70 to −80° C.

For cell lysis, half of a monkey tibia were smashed between two metal blocks covered with aluminum foil. The resulting powder was transferred immediately into a 50 mL centrifuge tube containing 20 mL cell lysis solution and mixed by inverting 3 times. The solution was homogenized quickly using tissue homogenizer PT 10/35 with generator PTA 10TS.

To precipitate proteins and DNA, 6.7 mL of protein-DNA precipitation solution was added to the lysate. The solution was mixed by inverting the tube 10 times and the tube was placed on ice for 15 minutes. After the 15 minute incubation on ice, the tube was centrifuged at 8,000 rpm (10,000×g) for 15 minutes. The precipitated proteins and DNA formed a tight pellet, allowing removal of the RNA-containing supernatant.

For RNA precipitation, the supernatant was poured into a clean 50 mL centrifuge tube containing 20 ml 100% isopropanol. The sample was mixed by inverting gently 50 times and incubated at room temperature for 10 minutes. Thereafter, the solution was centrifuged at 8,000 rpm (10,000×g) for 10 minutes to pellet the RNA. Most of the supernatant was poured off and the pellet with residual supernatant were transferred into a centrifuge tube. The sample was then centrifuged at 14,000×g for 5 minutes. The supernatant was removed with a pipette and the RNA pellet was washed several times with 70% ethanol. After the wash step, the RNA pellet was air dried for 5-10 minutes.

For RNA hydration, 0.1 mL RNase-free water was added to the pellet and allowed to rehydrate at room temperature for 10 minutes. The sample was mixed by pipetting up and down several times.

In order to remove residual DNA from the RNA isolated from bone, an on-column DNase digestion was performed using the RNEASY Mini Kit and the RNase-Free DNase Set (Qiagen, Hilden, Germany) according to the manufacturer's instructions.

EXAMPLE 2

This example shows how cDNA encoding the cDKK-4 protein was identified.

Total RNA was extracted from cynomolgus monkey tibia using the PURESCRIPT RNA Isolation Kit (Gentra Systems, Minneapolis, Minn.) as described in Example 1 followed by On-Column DNase Digestion as taught by Qiagen, Hilden, Germany. The resulting total RNA from bone was reverse transcribed using the SUPERSCRIPT First-Strand cDNA Synthesis Kit (Invitrogen, Carlsbad, Calif.) following the manufacturer's protocol.

Oligonucleotide primers were designed from the Dkk-4 human (hDkk-4) nucleotide sequence and used to identify cDNA encoding the cDkk-4. The 5' hDkk-4 forward primer (F2) was 5'-CAG GAG CCC CGG GAT TGA AGG ATG3' (SEQ ID NO:6) and the 3'hDkk-4 primer (R2) was 5'-GCA ATG TGG ATT CTT CTT TAT TTT GAA ATA TTT ATA GC-3' (SEQ ID NO:7). The hDKK-4 start codon is in boldfaced type.

One μL of the resulting cDNA templates was amplified in a 50 μL PCR reaction containing 1×PCR× Amplification Buffer (Invitrogen), 1×PCR× Enhancer Solution (Invitrogen), 1.5 mM $MgSO_4$, 200 μM each dNTP, 500 nM of each primer, and 2.5 units HIGH FIDELITY PLATINUM Taq (Invitrogen). The PCR cycling conditions consisted of an initial 6 minutes denaturation at 94° C., followed by 36 cycles of 94° C. for 1 minute, 60° C. for 1 minute, and 72° C. for 2 minutes. For the last cycle, the 72° C. extension time was 10 minutes. The resulting PCR products were sequenced on an ABI 310 Genetic Analyzer using ABI PRISM BIG DYE Terminator chemistry (Applied Biosystems, Foster City, Calif.) in both directions. The nucleotide sequence of cDKK-4 is shown in FIG. 1 and is set forth herein as SEQ ID NO:1. The amino acid sequence was deduced to be as set forth in SEQ ID NO:2 (FIG. 2).

EXAMPLE 3

The cynomolgus Dkk-4 cDNA identified in Example 2 was cloned as a 691 bp nucleotide fragment flanked by EcoRI restriction endonuclease sites as follows.

The cynomolgus-specific oligonucleotide primers were derived from the sequence obtained in Example 3. The forward primers were F 5'-GC GAATTC ACC ATG GCG GCG GCC GTC CTG CT-3' (SEQ ID NO:8) and FF 5'-GC GAATTC ACC ATG GCG GCG GCC GTC CTG CTG GGA CT-3' (SEQ ID NO:9). The reverse primers were R 5'-GC GAATTC TAG CTT TTC TAT TTT TTG GCA TAC TCG TAA CCG T-3' (SEQ ID NO: 10) and RR 5'-GC GAATTC TAG CTT TTC TAT TTT TTG GCA TAC TCG TAA CCG TGC ATG-3' (SEQ ID NO:11). The EcoRI site is underlined, the start codon for cDkk-4 is in bold-faced type, and the complement to the stop codon is in italics.

In the first step, total RNA isolated from monkey bone metaphysis was reversed transcribed into cDNA and the cDNA PCR amplified using the human F2 and R2 primers as in Example 2 for 30 cycles. Each reaction was performed in a 50 μL reaction mixture containing 1 μL of cDNA templates, 1×PCR× Amplification Buffer (Invitrogen), 1×PCR× Enhancer Solution (Invitrogen), 1.5 mM $MgSO_4$, 200 μM each dNTP, 500 nM each primer, and 2.5 units HIGH FIDELITY PLATINUM Taq (Invitrogen). Afterwards, 10 cycles of PCR amplification was performed using cynomolgus specific primer pairs F and R, FF and RR, F and RR, or PF and R. The PCR cycling conditions consisted of an initial 4 minute denaturation step at 95° C., followed by 10 cycles of 95° C. for 1 minute, 60° C. for 1 minute and 72° C. for 2 minutes. For the last cycle, the 72° C. extension time was 10 minutes. The preferred primer pair was FF and RR.

The 691 bp PCR reaction product following amplification with the FF and RR primers was purified using the QIAGEN PCR purification kit (Qiagen) according to the manufacturer's instructions. The purified PCR product was digested with EcoRI and then electrophoresed on an agarose gel stained with ethidium bromide to remove unwanted digestion products. The 691 bp PCR product was eluted from the agarose gel using the QIAQUICK Gel Extraction kit (Qiagen) following the manufacturer's instructions. The gel purified 691 bp PCR product was then ligated into EcoRI digested and phosphatase-treated pcDNA3.1/Myc-His plasmid vector (5.5 kb; Invitrogen, Carlsbad, Calif.) using either the Takara Ligation kit (Takara Bio Inc., Shiga, Japan) or the T4 DNA Ligase kit (Roche Diagnostics, Pleasanton, Calif.) to make plasmid pcDNA3.1/Dkk-4/Myc-His. The relevant features of pcDNA3.1/Myc-His include a multiple cloning site downstream from a cytomegalovirus (CMV) immediate early promoter which is a constitutive promoter that enables DNA inserted into the multiple cloning site to be transcribed into RNA, an ampicillin gene for selection of transformants in bacteria, and a neomycin gene for selection of transfectants in mammalian cells.

About 3 μL of the ligation reaction was then used to transform 70 μL of MAX EFFICIENCY DHα5 *E. coli* using the manufacturer's instructions. Eighteen colonies were randomly picked after transformation and screened for clones containing the 691 bp PCR reaction product in the direct orientation. In the direct orientation, the 5' end of the Dkk-4 coding region is operably linked to the upstream CMV promoter such that the RNA transcript produced therefrom can be translated into the Dkk-4 protein. To screen for colonies containing the 691 bp PCR product in the direct orientation it was convenient to digest plasmid DNA isolated from various clones with ApaI followed by electrophoresis of the digested DNA on agarose gels stained with ethidium bromide. The 691 bp PCR product contains an ApaI site about 106 bp downstream of the start codon and the plasmid vector contains an ApaI site about 45 bp downstream of the EcoRI cloning site. In the direct orientation, an ApaI digest produces a 612 bp DNA fragment and a 5.6 kb DNA fragment whereas in the indirect orientation, an ApaI digest produces a 151 bp DNA fragment and a 6.1 kb DNA fragment.

Clones 2, 7, 12, and 14, each containing the 691 bp PCR product in the direct orientation, were sequenced using an ABI 310 Genetic Analyzer and ABI PRISM BIG DYE Terminator chemistry. Each clone was sequenced using the FF PCR primer, the RR PCR primer, sequencing primer Fseq 5'-GGG ACA CTC TGC ATG AAT GAT G-3' (SEQ ID NO:12), and sequencing primer Rseq 5'-TGC CAT CTT GCT CAT CAA GCT-3' (SEQ ID NO:13). The sequencing reactions consisted of an initial denaturation at 96° C. for 2 minutes followed by 25 cycles of 96° C. for 10 seconds, 50° C. for 5 seconds, and 60° C. for 4 minutes in a thermocycler followed by electrophoresis on the ABI 310 Genetic Analyzer. Clone 14 was determined to contain the nucleotide sequence encoding cDkk-4 was identified which had the nucleotide sequence shown in FIG. 1 (SEQ ID NO:1) and the deduced amino acid sequence shown in FIG. 2 (SEQ ID NO:2). The plasmid is designated herein as pcDNA3.1/Dkk-4/Myc-His-direct14.

EXAMPLE 4

Expression of Dkk-1, Dkk-2, Dkk-4, LRP5, and LRP6 in a variety of human tissues was compared to expression in monkey bone using the TAQMAN Gold RT-PCR Kit (Applied Biosystems Inc., Foster City, Calif.). The human tissues are listed in Table 1.

TABLE 1

| | |
|---|---|
| 1 | Adrenal gland |
| 2 | Bone marrow |
| 3 | Brain cerebellum |
| 4 | Brain (whole) |
| 5 | Heart |
| 6 | Kidney |
| 7 | Liver |
| 8 | Lung |
| 9 | Prostrate |
| 10 | Salivary gland |
| 11 | Skeletal muscle |
| 12 | Spleen |
| 13 | Testis |
| 14 | Thymus |
| 15 | Thyroid |
| 16 | Trachea |
| 17 | Uterus |
| 18 | Colon |
| 19 | Small intestine |
| 20 | Aorta/heart |
| 21 | Placenta |
| 22 | Mammary gland |
| 23 | Stomach |
| 24 | Ovary |
| 25 | Cervix |
| 26 | Bladder |

For analyzing Dkk-1 expression, the Dkk-1 primers were human/monkey Dkk-1-F 5'-GAA GTT CAA GTG TGT ACC AAG CAT AG-3' (SEQ ID NO: 14) and Dkk-1-R 5'-AGGTGTGAAGCCTAGAAGAATTACTGG-3' (SEQ ID NO:15) and the Dkk-1 probe was human/monkey Dkk-1-FAM 5'-TTG ATG GTG ATC TTT CTG TAT CCG GCA AG-3' (SEQ ID NO:16).

For analyzing Dkk-2 expression, the Dkk-2 primers were human Dkk-2-F 5'-CTG TAT CCC AGT TAC TGA AAG CAT CT-3' (SEQ ID NO:17) and Dkk-2-R 5'-ATG ACC GTG GTT TCG ATC TCT G-3' (SEQ ID NO:18) and the Dkk-2 probe was human Dkk-2-FAM 5'-CCT CAC ATC CCG GCT CTG OAT GGT A-3' (SEQ ID NO:19).

For analyzing Dkk-4 expression, the Dkk-4 primers were human Dkk-4F 5'-GAT GTT TGT ACT ACG ATG GAA GAT GC-3' (SEQ ID NO:20) and Dkk-4R 5'-GCC CAG TTG TTC CTT CTG CA-3' (SEQ ID NO:21) and the Dkk-4 probe was human Dkk-4-FAM 5'-CAG CTT GAT GAG CAA GAT GOC ACA CA-3' (SEQ ID NO:22).

For analyzing LRP5 expression, the LRP5 primers were human LRP5-F 5'-TCT GGG CCT GAC CAT CCT T-3' (SEQ ID NO:23) and LRP5-R 5'-TCC ACA CGC TCG ATC ATC TG-3' (SEQ ID NO:24) and the LRP5 probe was human LRP5-FAM 5'-CAA GCA TCT CTA CTG GAT CGA CCG CC-3' (SEQ ID NO:25).

For analyzing LRP6 expression, the LRP6 primers were human LRP6-F 5'-TTC TTC AAG CAC CAA AGG CAC-3' (SEQ ID NO:26) and LRP6-R 5'-CCA TAG TGT AAT GTG ATC GCT CTG T-3' (SEQ ID NO:27) and the LRP6 probe was human LRP6-FAM 5'-TGC AAT TTT GAA CCC TCC ACC ATC CC-3' (SEQ ID NO:28).

Each probe had the fluorescent reporter dye FAM covalently linked to the 5' end of the probe and the TAMARA dye quencher covalently linked to the 3' end of the probe.

In the first step, RNA was extracted from each of the tissue samples and reverse transcribed as follows.

Total RNA was extracted from the tissues and monkey bone using methods known in the art.

For each reverse transcription reaction, a 100 μL reaction mixture was prepared which contained about 7.6 ηg of RNA in 1×RT buffer, 5.5 mM $MgCl_2$, 500 μM each dNTP, 2.5 μM random hexamers, 0.4 units/μL RNAse inhibitor, and 1.25 units/μL MULTISCRIBE RT enzyme. Ten μL aliquots were dispensed into appropriate wells of a PCR reaction plate. The wells were covered and the reverse transcription was carried out on a 9700 Cycler at 25° C. for 10 minutes, 48° C. for 30 minutes, and then 95° C. for 5 minutes to stop the reaction.

Afterwards, 40 μL of a PCR reaction mix was added to the above reverse transcription reaction to provide a reaction mixture containing 1×TAQMAN Buffer A, 5.5 mM $MgCl_2$, 200 μM each of dATP, dCTP, dGTP, and dUTP, 100 μM each of the forward and reverse primers and the probe, 0.01 units/μL AMPERASE UNG, and 0.025 units/μL AMPLITAQ GOLD. The PCR reaction was performed on a 7700 Sequence Detector beginning with a 2 minute incubation at 50° C. (UNG incubation) followed by PCR. Detection was plate read (endpoint).

Figure 6:
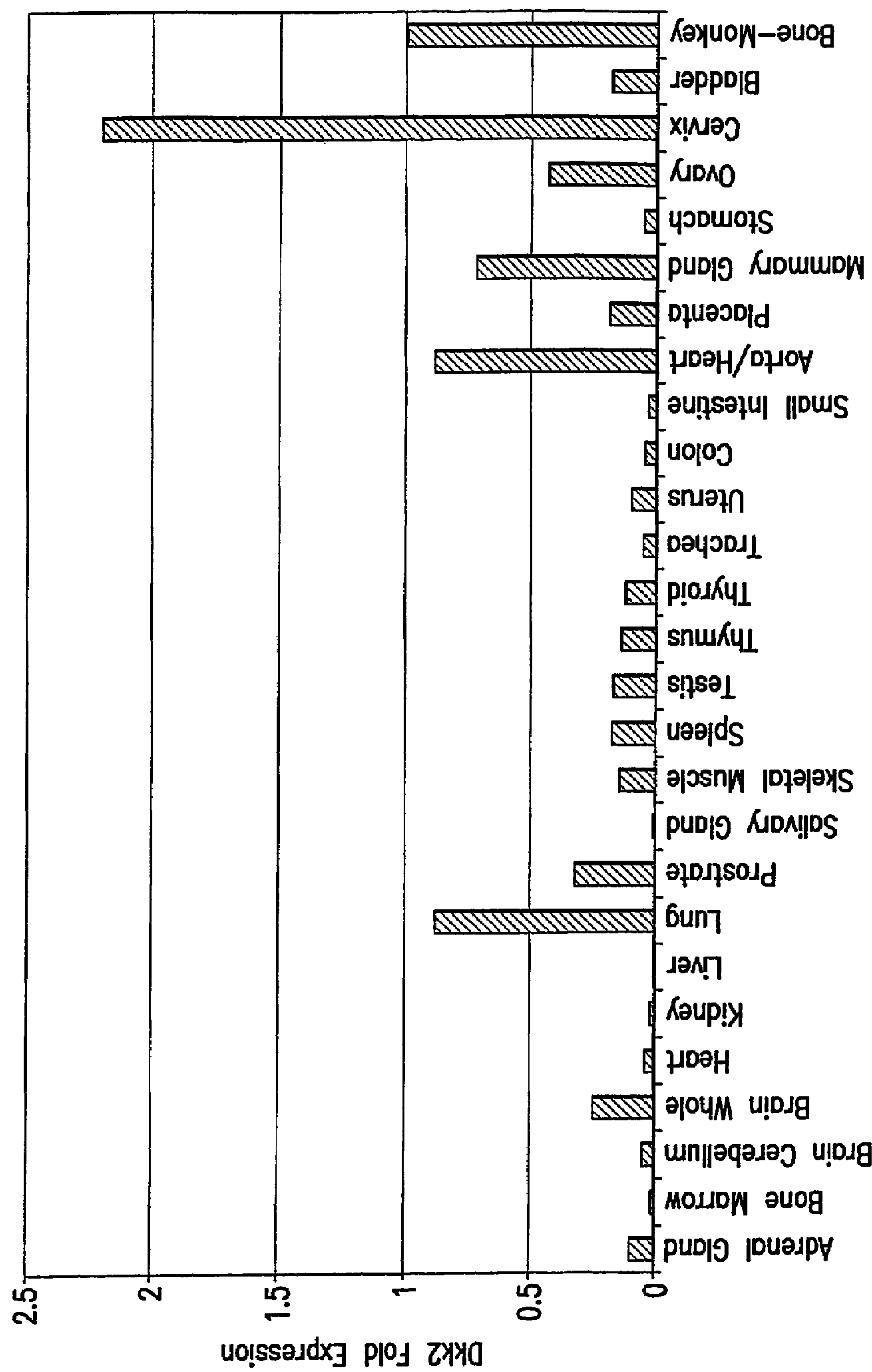
FIG. 6 shows a bar graph of Dkk-2 gene expression in a variety of human tissues compared to Dkk-2 expression in monkey bone. Expression was measured by TAQMAN RT-PCR analysis of cDNA prepared from RNA isolated from the tissue.
Figure 7:
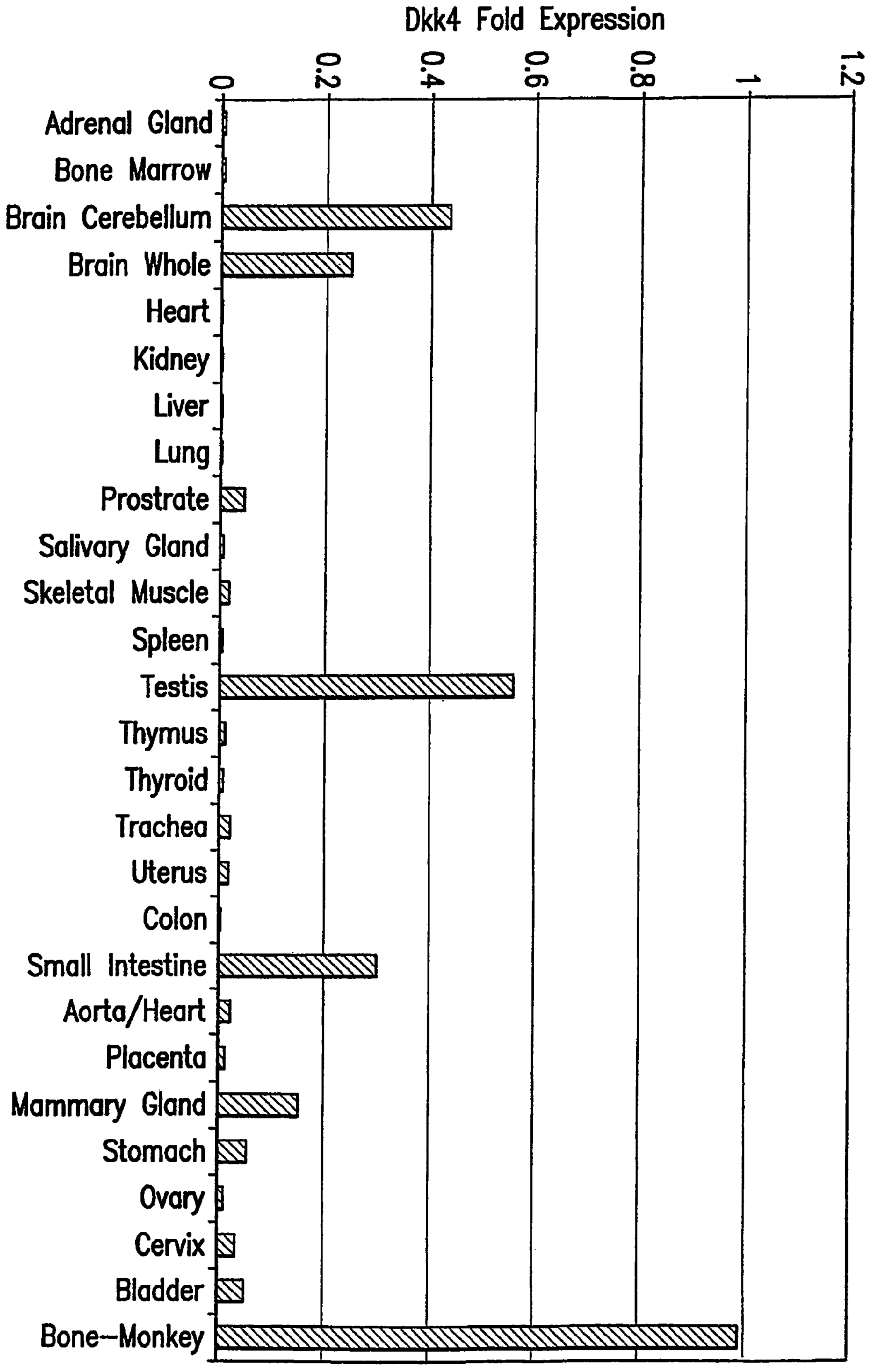
FIG. 7 shows a bar graph of Dkk-4 gene expression in a variety of human tissues compared to Dkk-4 expression in monkey bone. Expression was measured by TAQMAN RT-PCR analysis of cDNA prepared from RNA isolated from the tissue.
Figure 8:
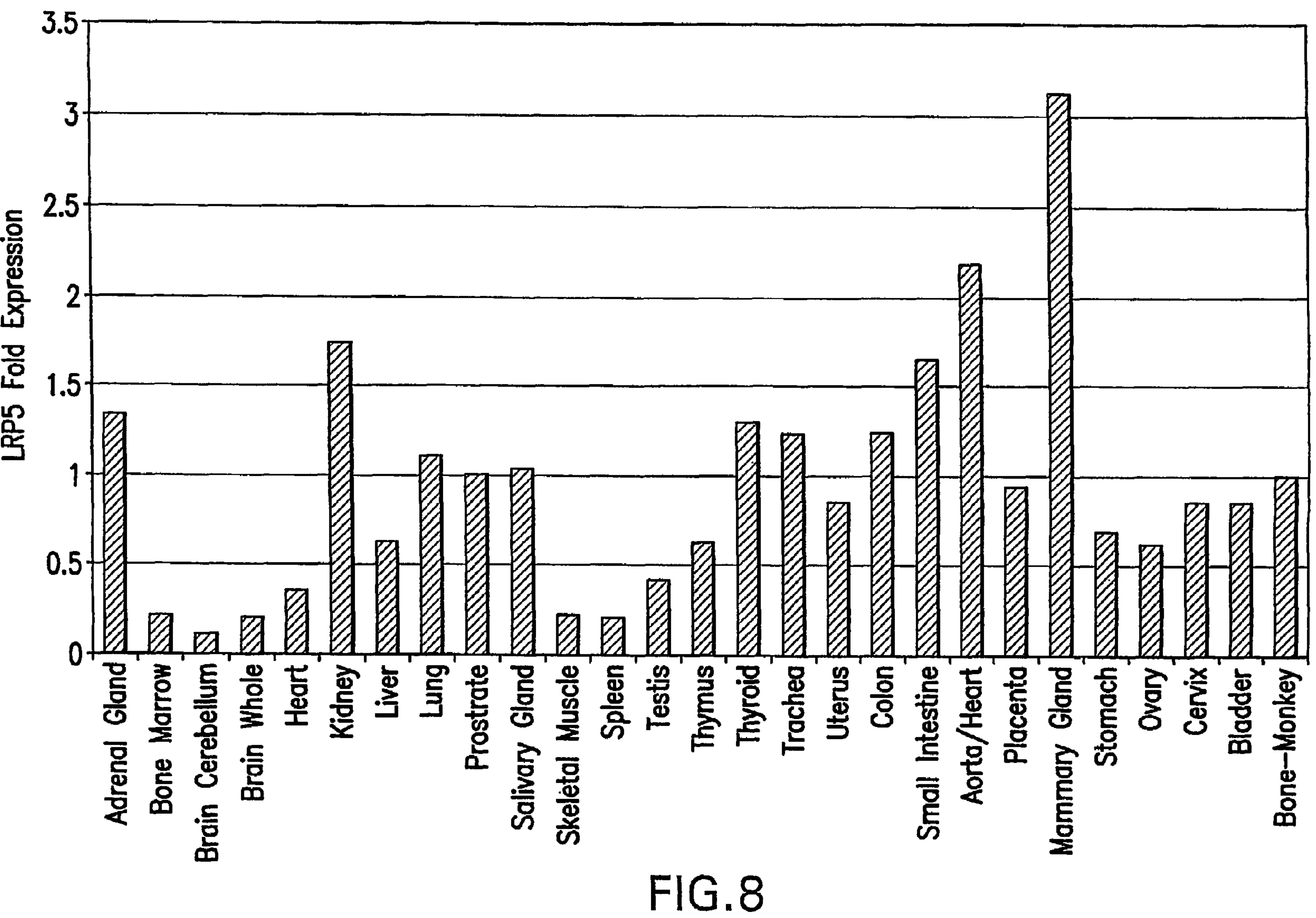
FIG. 8 shows a bar graph of LRP5 gene expression in a variety of human tissues compared to LRP5 expression in monkey bone. Expression was measured by TAQMAN RT-PCR analysis of cDNA prepared from RNA isolated from the tissue.
Figure 9:
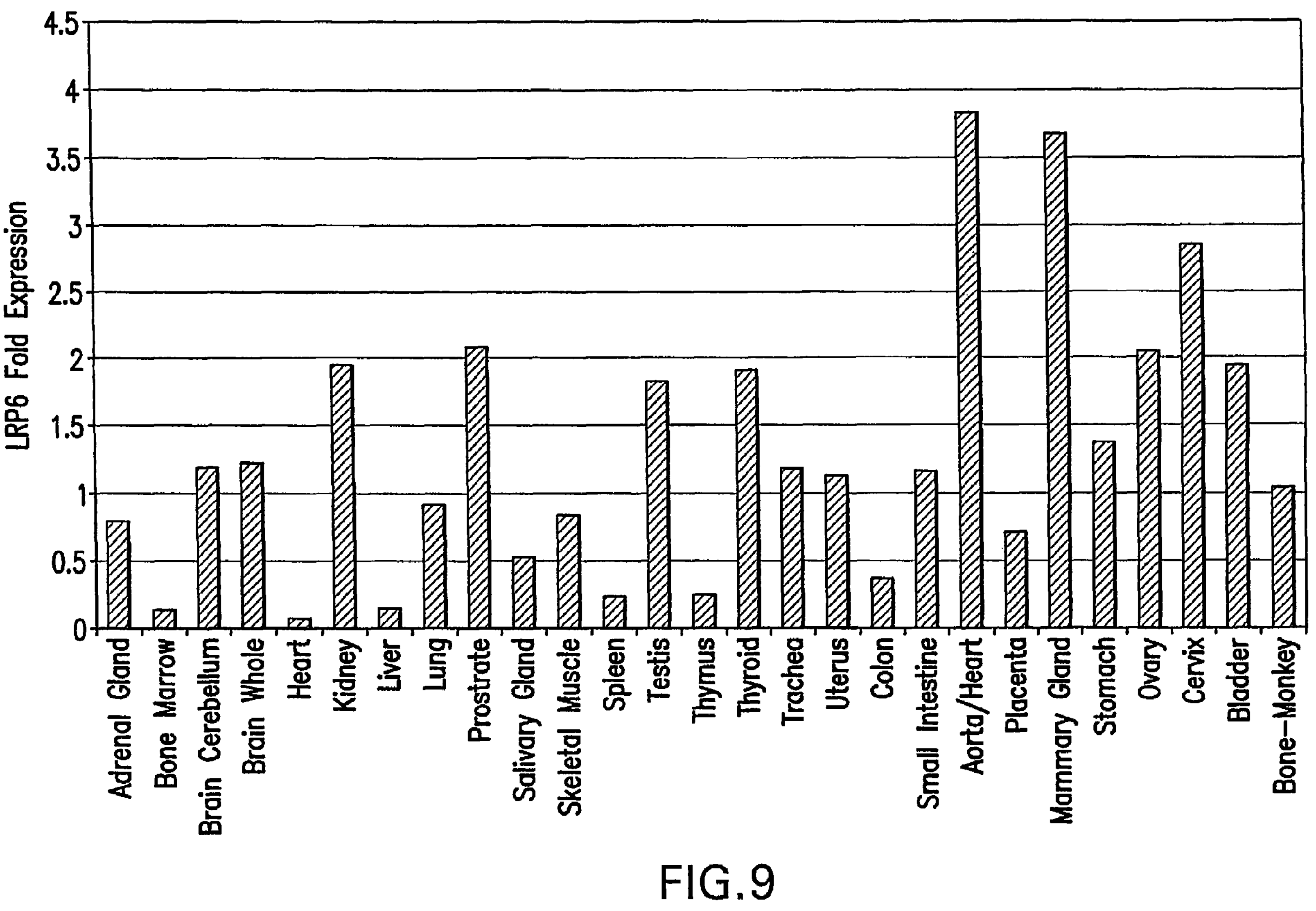
FIG. 9 shows a bar graph of LRP6 gene expression in a variety of human tissues compared to LRP6 expression in monkey bone. Expression was measured by TAQMAN RT-PCR analysis of cDNA prepared from RNA isolated from the tissue.

The results are summarized in FIGS. 5-9. FIG. 5 shows that Dkk-1 is expressed primarily in human placenta, cervix, and bladder tissue with some expression in monkey bone and a little expression in the human prostrate tissue. FIG. 6 shows that Dkk-2 is expressed primarily in human lung, prostrate, aorta/heart, mammary gland, ovary, and cervix tissue; monkey bone tissue; and, to a lesser extent in the remaining human tissues. FIG. 7 shows that Dkk-4 is expressed primarily in human brain cerebellum, whole brain, testis, small intestine, and mammary tissues with significant expression in monkey bone. FIGS. 8 and 9 show that LRP5 and LRP6 are expressed in most human tissues including monkey bone. These results suggest that Dkk-4 has a role in regulating bone formation in bone tissue and further suggest that identifying analytes which inhibit or suppress Dkk-4/LR5 interactions will stimulate bone formation in bone tissue.

EXAMPLE 5

This example describes a method for making polyclonal antibodies specific for the cDkk-4 protein.

cDkk-4 protein is produced in *E. coli* transformed with pcDNA3.1/Dkk-4/Myc-His-direct14. Antibodies are generated in New Zealand white rabbits over a 10-week period. The cDkk-4 protein is emulsified by mixing with an equal volume of Freund's complete adjuvant and injected into three subcutaneous dorsal sites for a total of 0.1 mg cDkk-4 protein per immunization. A booster containing about 0.1 mg cDkk-4 emulsified in an equal volume of Freund's incomplete adjuvant is administered subcutaneously two weeks later. Animals are bled from the articular artery. The blood is allowed to clot and the serum collected by centrifugation. The serum is stored at −20° C.

For purification, cDkk-4 protein is immobilized on an activated support. Antisera is passed through the sera column and then washed. Specific antibodies are eluted via a pH gradient, collected, and stored in a borate buffer (0.125M total borate) at −0.25 mg/mL. The anti-cDkk-4 antibody titers are determined using ELISA methodology with free cDkk-4 bound in solid phase (1 pg/well). Detection is obtained using biotinylated anti-rabbit IgG, HRP-SA conjugate, and ABTS.

EXAMPLE 6

This example describes a method for making monoclonal antibodies specific for the cDkk-4 protein.

BALB/c mice are immunized with an initial injection of about 1 μg of purified cDkk-4 protein per mouse mixed 1:1 with Freund's complete adjuvant. After two weeks, a booster injection of about 1 μg of the antigen is injected into each mouse intravenously without adjuvant. Three days after the booster injection serum from each of the mice is checked for antibodies specific for the cDkk-4 protein.

The spleens are removed from mice positive for antibodies specific for cDkk-4 protein and washed three times with serum-free DMEM and placed in a sterile Petri dish containing about 20 mL of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 mL 0.17 M ammonium chloride and placed on ice for several minutes. Then 5 mL of 20% bovine fetal serum is added and the cells pelleted by low-speed centrifugation. The cells are then resuspended in 10 mL DMEM and mixed with mid-log phase myeloma cells in serum-free DMEM to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES, pH 8.1, at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 μM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the cDkk-4 protein. One hundred μL of supernatant from each well is added to a corresponding well on a screening plate and incubated for 1 hour at room temperature. After incubation, each well is washed three times with water and 100 μL of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 μL of 1 M HCl is added to stop the reaction and the absorbance of the wells is measured at 490 nm. Cultures that have an absorbance greater than the control wells are removed to two $cm^2$ culture dishes, with the addition of normal mouse spleen cells in HAT medium. After a further three days, the cultures are re-screened as above and those that are positive are cloned by limiting dilution. The cells in each two $cm^2$ culture dish are counted and the cell concentration adjusted to $1\times10^5$ cells per mL. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 $cm^2$ cultures and provided with normal mouse spleen cells. This cloning procedure is repeated until stable antibody producing hybridomas are obtained. The stable hybridomas are progressively expanded to larger culture dishes to provide stocks of the cells.

Production of ascites fluid is performed by injecting intraperitoneally 0.5 mL of pristane into female mice to prime the mice for ascites production. After 10 to 60 days, $4.5\times10^6$ cells are injected intraperitoneally into each mouse and ascites fluid is harvested between 7 and 14 days later.

EXAMPLE 7

In this example of a cell-based reporter assay, a signaling system in the mouse fibroblast NIR3T3 cell line is used to identify compounds which interfere with binding of cDkk-4 protein to human LRP5. The signaling system is based on Wnt signaling using a reporter gene under the control of an LEF-1-responsive promoter (Boyden et al., N. Eng. J. Med. 346: 1513-1521 (2002); Mao et al., Mol. Cell 7: 801-809 (2001); Hsu et al., Mol. Cell. Biol. 18: 4807-4818 (1998)).

Expression plasmids encoding LEF-1 protein, Wnt-1 protein, and LRP5 are constitutively expressed from a cytomegalovirus (CMV) promoter, and the reporter gene luciferase under the control of an LIF-1 responsive promoter are disclosed in Boyden et al., supra; Mao et al., supra; Hsu et al., supra. cDkk-4 is also constitutively expressed from a CMV promoter. Expression plasmid pcDNA3.1/Dkk-4/Myc-His-direct14 is used to express cDkk-4.

NIH3T3 cells are cultured at 37° C. in Dulbecco's modified Eagle medium supplemented with 5% fetal bovine serum in a 5% $CO_2$ atmosphere. Transient transfections are performed by any transfection method known in the art including, but not limited to, the DEAE-dextran-chloroquine procedure, CaCl precipitation procedure, electroporation, FuGENE (Roche Applied Sciences), and LIPOPECTIN (Invitrogen) procedure. As a control for efficiency of transfection a β-galactosidase control expression plasmid is included in the transfections.

Plasmids encoding LEF-1 protein, the luciferase as the reporter gene operably linked to the LEF-1 responsive promoter, and green fluorescent protein are transfected into NIH3T3 cells seeded in 24-well plates at about $5\times10^4$ cells/well. Plasmids encoding LRP5, Wnt-1, and cDkk-4 are also transfected into the cells. The total amount of DNA transfected is preferably about 0.5 μg per well. After transfection, the cells are incubated in medium containing the analyte to be tested for its ability to interfere with binding of the cDkk-4 protein to LRP5. Controls without the analyte are routinely performed. After about 24 hours post-transfection, the cells are lysed and the levels of luciferase activity and green fluorescent protein are measured (Li et al. EMBO J. 18: 4233-4240 (1999); Yuan et al., J. Biol. Chem. 274: 30419-30423 (1999)). The luciferase activity is normalized according to the green fluorescent protein level to account for variations in the efficiency of transfection.

An increase in luciferase activity in transfected cells incubated with a particular analyte relative to controls which do not contain the analyte indicates that the analyte interferes with the inhibitory effect of cDkk-4 on Wnt-1 signaling. Analytes which are identified in the above assay as being capable of interfering with the binding of the cDkk-4 protein to LRP5 are candidates for further evaluation on their ability to stimulate bone formation in vivo or induce pluripotent cells to differentiate along an osteoblastic linage.

EXAMPLE 8

This examples describes a cell-binding method for identifying analytes which interfere with the ability of cDkk-4 protein to bind a Dkk receptor on the surface of a cell. To identify interfering analytes, recombinant cells, which express LRP5 on the surface, are incubated in medium containing labeled cDkk-4 protein. The cells are then evaluated for bound cDkk-4 protein HEK293T cells are transfected with the LRP5 expression vector in which the human LRP5 is constitutively expressed from a cytomegalovirus (CMV) promoter. The LRP5 expression vector comprises the human LRP5 cDNA cloned into the pcDNA3 expression vector (Invitrogen) as taught in Gong et al., Cell 107: 513-523 (2001). The labeled cDkk-4 is a cDkk-4-AP fusion polypeptide which is provided in conditioned medium produced by transient transfection of HEK293T cells with pcDNA3.1/Dkk-4/Myc-His-direct14 in which the alkaline phosphatase (human placental alkaline phosphatase) gene is cloned in frame at the 3' end of the cDkk-4 cDNA in pcDNA3.1/Dkk-4/Myc-His-direct14.

The FuGENE transfection protocol (Roche Applied Sciences) is used according to the manufacturer's instructions. Cells are plated the day before the transfection at a density to give about 50-80% confluence on the day of the transfection. About $1\text{-}3\times10^5$ cells in 2 mL of Dulbecco's modified Eagle's medium containing 5% fetal calf serum or 10% horse serum in a 35 mm culture dish (or 6-well plate) will achieve this density after overnight incubation at 37° C. In a small sterile tube, add sufficient serum-free medium as diluent for FuGENE 6 Transfection Reagent, to a total volume of 100 μL. About 3 to 6 μL of FuGENE 6 Reagent is added directly into this medium. Tap gently to mix. About 1-2 μg of DNA (LRP5 expression vector) solution (about 0.02-2.0 μ/μL) is added to the prediluted FuGENE 6 Reagent above. Use a total volume of DNA solution between 0.5-50 μL. Gently tap the tube to mix the contents. Incubate for a minimum of about 15 minutes at room temperature. The complex mixture is added to the cells dropwise and distributed around the well. The cells are returned to the incubator and incubated for 48 hours. After 48 hours, the cell binding assay is performed.

The medium is removed from the cells and medium containing cDkk-4-AP fusion polypeptide and an analyte to be tested for interfering with binding of cDkk-4 protein to LRP5 is added to the cells. Controls consist of medium containing cDkk-4AP only, medium containing the analyte only, and medium containing neither cDkk-4-AP or the analyte. Detection of cDkk-4-AP fusion polypeptide bound to LRP5 on the cell surface is by measuring alkaline phosphatase activity on the cell surface. This can be done by staining the cells with FAST RED reagent (Roche Applied Sciences). Cells with cDkk-4-AP bound to LRP5 on the surface stain red with the reagent. A decrease in alkaline phosphatase activity in wells containing a mixture of the cDkk-4-AP fusion protein and an analyte compared to controls containing the cDkk-4-AP fusion protein without the analyte indicates that the analyte interferes with the binding of Dkk-4 to LRP5.

EXAMPLE 9

This example illustrates an osteoblast differentiation assay for identifying analytes which interferes with Dkk-4 protein inhibition of differentiation of pluripotent mesenchymal cells along the osteoblastic lineage in vitro.

Katagiri et al., J. Cell Biol. 127: 1755-1766 (1994) and Yamaguchi et al., Biochem. Biophys. Res. Commun. 220: 366-371 (1996) have shown that adding exogenous growth factors to pluripotent marrow stromal cells induces the cells along an osteoblastic lineage. Gong et al. (Cell 107: 513-523 (2001) show that adding 300 ng/ml of BMP2 to the pluripotent mesenchymal cells C3H10T1/2 and ST2 results in expression of the osteoblastic markers alkaline phosphatase (ALP), Bglap, and Runx2. Gong et al. further show that ALP activity can be induced in C3H10T1/2 and ST2 cells by transfecting the cells with vectors expressing LRP5 and Wnt and that ALP activity can be induced in ST2 cells that are stably expressing LRP5 by transfecting the cells with a vector expressing Wnt. Thus, the Wnt signaling pathway is involved in differentiation of pluripotent cells along an osteoblast lineage. Therefore, because Dkk-1 and Dkk-4 can inhibit the Wnt signaling pathway by binding LRP5, the osteoblast differentiation assay of Gong et al. can be adapted to an assay for identifying analytes which inhibit or suppress Dkk-4 inhibition of osteoblast differentiation.

The LRP5 expression vector comprising the human LRP5 cDNA cloned into the pcDNA3 expression vector and the Wnt expression vector comprising the Wnt3 cDNA cloned into the pcDNA3 vector are constructed as taught in Gong et al., Cell 107: 513-523 (2001). Expression plasmid pcDNA3.1/Dkk-4/Myc-His-direct14 is used to express cDkk-4.

C3H10T1/2 or ST2 cell lines are cultured in α-MEM and RPMI medium, respectively, supplemented with 10% heat-inactivated fetal bovine serum at 37° C. in a 5% $CO_2$ atmosphere. For treatment or transient transfection, cells are plated at $2\times10^4$/cm$^2$ and 24 hr later, treatment or transfections were carried out as indicated below.

Cells are plated in 24 well plates and transiently transfected with all three constructs (about 1 μg/construct) using FuGENE 6. When required, transfection controls are used which comprise the empty pcDNA3 vector. ST2 stably transfected cell lines are maintained in the corresponding culture medium supplemented with G418 (500 μg/ml). About sixteen hours after transfection, the cells are washed, cultured in media containing 2% fetal bovine serum, and cultured either with or without a test analyte for an additional 48 hours.

ALP activity is determined in cell lysates by the Alkaline Phosphatase Opt kit (Roche Molecular Biochemicals). Cell lysates are analyzed for protein content by using the micro-BCA Assay kit (Pierce) and ALP activity is normalized for total protein concentration.

ALP activity detected in the presence of a test analyte indicates that the analyte interferes with binding of the cDkk-4 protein to the LRP5 receptor which allows Wnt to induce differentiation along the osteoblast lineage. Conversely, the absence of ALP activity indicates that the analyte does not interfere with binding of the cDkk-4 protein to LRP5 and there is no Wnt induced differentiation along the osteoblast lineage.

EXAMPLE 10

This example provides a cell-based assay for identifying analytes that interfere with binding between Dck-4 and LRP5 using cDkk-4 labeled with the lanthanide europium.

Standard cell culture medium is Dulbecco's modified Eagle's medium (DMEM) containing 10% fetal bovine serum (FBS) and penicillin/streptomycin (Gibco BRL, Invitrogen, Gaithersburg, Md.). HEK 293 cells overexpressing human LRP5 are generated by transfecting DNA encoding human LRP5 under the control of a heterologous constitutive promoter into HBEK-293 cells. Recombinant cells stably transfected with DNA encoding LRP5 are selected with hygromycin (100 μg/mL).

DNA encoding Dkk-4 is inserted into a baculovirus vector adjacent to and in frame to a nucleotide sequence encoding polyhistidine. Baculovirus-susceptible insect cells are infected with the recombinant baculovirus vector to produce cDkk-4 comprising a polyhistidine sequence at the carboxy terminus. The polyhistidine-tagged cDkk-4 is purified using nickel column chromatography and labeled with europium chelate N1-isothiocyanate (Perkin Elmer, Boston, Mass.).

The cDkk-4-LRP5 binding assays are carried out as follows. The recombinant HEK 293 cells stably overexpressing human LRP5 are plated into the wells of white/white, 384-well, PDL plates (BD Biosciences, San Jose, Calif.). Each well contains cells and 30 μL of medium containing 2.5% FBS. The next day, to each well, 250 nL of an analyte is added (high concentration copy, CyBi Disk) for final a concentration of about 30 μM. Next, 5 μL of Eu-cDkk-4 is added to each of the wells (CyBi Well, 0.1 nM final concentration). After incubating at 37° C. for 30 minutes, the wells are washed four times each with a wash solution (TBS containing 0.02% Tween-20). After the final wash, 20 μL of Enhancement Solution (Perkin Elmer) is added to each of the wells. After incubating the wells in Enhancement Solution for 30 minutes at room temperature, the wells are vortexed and the time resolved fluorescence from the wells is read using the LEAD-SEEKER, a CCD-based optical imaging instrument that can measure fluorescence (Amersham Biosciences, Piscataway, N.J.).

To determine whether an analyte's inhibitory effect on the binding of cDkk-4 to human LRP5 is specific or non-specific, counterscreens are performed using either a wheat germ agglutinin-biotin/steptavidin (WGA) assay or a human TNFα assay in the same recombinant cells overexpressing the human LRP5. The WGA assay is performed with the above recombinant HEK 293 cells incubated with the analyte and wheat germ agglutinin linked to biotin (WGA-biotin; Biomeda Corp.) and streptavidin labeled with europium (Eu-streptavidin; Perkin Elmer) instead of the Eu-cDkk-4. The amount of the WGA-biotin/Eu-streptavidin complex bound in the presence and absence of the analytes is measured. The TNFα assay is performed as above except that the recombinant HEK 293 cells are incubated with the analyte and the TNFα labeled with europium (Eu-TNFα; Perkin Elmer) instead of Eu-cDkk-4. The amount of TNFα bound to the cells in the presence and absence of the analytes was measured.

EXAMPLE 11

This example provides a cell-based assay for identifying analytes that interfere with binding between Dkk-4 and LRP5 using a fusion protein comprising the cDkk-4 fused to the Green fluorescence protein.

Recombinant cells stably transfected with DNA encoding LRP5 were produced as previously described.

Fusion proteins comprising the cDkk-4 fused to the Green fluorescence protein (GFP) were prepared as follows. DNA encoding cDkk-4 was cloned in-frame with DNA encoding the GFP using expression plasmid pEGFP-N2 (Clontech, Palo Alto, Calif.) to produce a DNA encoding the fusion protein cDkk-4-GFP. An expression plasmid encoding the cDkk-4-GFP fusion protein was transfected in HEK293 cells. The transfected cells were incubated at 37° C. in 5% $CO_2$. Seventy-two hours later, medium was removed from the cells, sterile filtered, and supplemented with 20 mM Hepes-buffer (pH 7.5) to produce conditioned medium.

The cDkk-4-GFP fusion protein-LRP5 binding assays were as follows. Recombinant HEK-293 cells stably overexpressing human LRP5 were plated into the wells of a 384-well tissue culture plate (Corning) at a concentration of about 6,000 cells/well. Each well contained 45 μL of phenol red-free DMEM containing 2.5% FBS. To each well, an analyte was added. One minute later, 5 μL of conditioned medium containing 10 μM DRAQ5 nuclear stain was added to each well and the wells incubated at 37° C. for 25 minutes. Imaging and evaluation of cDkk-4-GFP fusion protein binding to the recombinant cells overexpressing LRP5 was determined using an INCell 3000 imager (Amersham).

EXAMPLE 12

This examples provides a cell-based functional assay for determining whether an analyte can activate the Wnt pathway by interfering with the binding of Dkk-4 to LRP5.

Recombinant cells stably transfected with DNA encoding LRP5 were produced as previously described.

Cells are seeded in DMEM containing 2.5% FBS (80 μL) into the wells of a multi-well tissue culture plate and transfected with pTOPFLASH (a plasmid vector comprising the luciferase gene operably linked to the thymidine kinase minimal promoter adjacent to TCF/LEF binding site; Upstate Biotechnology, Lake Saranac, N.Y.) and pTK-renilla (Promega Corp., Madison, Wis.) using FUGENE6 (Roche) in OPTIMEM medium (Gibco BRL). The plasmid pTK-renilla is included for normalizing transfection efficiency.

Twenty-four hours post-transfection, an analyte is added to each of the wells. Afterwards, rhDkk1 and a Wnt-ligand (for example, Wnt3A or Wnt1) are added to each of the wells. Wnt ligand can be provided either by using purified Wnt ligand, conditioned medium obtained from cells transfected with a plasmid encoding Wnt ligand, or by co-transfecting the cells a plasmid comprising DNA encoding the Wnt ligand with the above plasmids. CDkk-4 can be provided either by using purified cDkk-4 protein, conditioned medium obtained from cells transfected with a plasmid encoding cDkk-4, or by co-transfecting the cells a plasmid comprising DNA encoding the cDkk-4 with the above plasmids. About 6 to 48 hours after the analytes had been added to the wells, the recombinant cells are lysed by adding 20 μL of 1×Passive Lysis buffer (Promega). Luciferase activities can be measured in a VICTOR3 plate reader (Perkin Elmer).

An increase in luciferase expression indicates that the analyte being tested interferes with binding of cDkk-4 to LRP5. The interference enables the LRP5 to interact with the Wnt ligand and Frizzled on the cell membrane, which in turn activates disheveled in the cell cytoplasm, which in a series of intracellular events causes β-catenin to accumulate in the cytoplasm. The β-catenin then translocates to the nucleus where it interacts TCF transcription factors to activate transcription of the luciferase gene provided by pTOPFLASH.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An isolated nucleic acid molecule comprising a nucleotide sequence encoding a cynomolgus monkey Dickkopf-4 (cDkk-4) protein comprising the amino acid sequence as set forth in SEQ ID NO:2.

2. The isolated nucleic acid of claim 1 wherein the nucleic acid is a DNA.

3. The isolated nucleic acid of claim 1 wherein the nucleic acid is an RNA.

4. The isolated nucleic acid of claim 1 wherein the nucleic acid is a cDNA.

5. The isolated nucleic acid of claim 1 wherein the nucleic acid has the nucleotide sequence as set forth in SEQ ID NO:1.

6. An isolated protein comprising the amino acid sequence as set forth in SEQ ID NO:2.

7. A method for producing a cynomolgus monkey Dickkopf-4 (cDkk-4) protein comprising the amino acid sequence as set forth in SEQ ID NO:2 which binds a low-density lipoprotein receptor protein 5 (LRP5) comprising:

(a) providing a nucleic acid encoding the cDkk-4 protein operably linked to a heterologous promoter;

(b) introducing the nucleic acid into a cell to produce a recombinant cell; and (c) culturing the recombinant cell under conditions which allows expression of the cDkk-4 protein to produce the cDkk-4.

8. A method for determining whether an analyte is an antagonist of Dickkopf4 (Dkk-4) binding comprising:

(a) providing a polypeptide comprising the extracellular domain of a Dkk-4 receptor;

(b) contacting the polypeptide with a cynomolgus monkey Dkk-4 (cDkk-4)protein comprising the amino acid sequence as set forth in SEQ ID NO:2 and the analyte; and (c) determining whether binding of the cDkk-4 to the polypeptide is decreased in the presence of the analyte, wherein a decrease in the binding indicates that the analyte is an antagonist of cDkk-4 binding.

9. The method of claim 8, wherein the Dkk-4 receptor is low-density lipoprotein receptor related protein 5 (LRP5) or low density lipoprotein receptor related protein 6 (LRP6).

10. The method of claim 8, wherein the Dkk-4 receptor is kremen 1 or kremen2.

11. The method of claim 8 wherein the cDkk-4 is labeled.

12. The method of claim 8 wherein the cDkk-4 is a fusion protein.

* * * * *